United States Patent [19]

Baxter, Jr. et al.

[11] 4,093,849
[45] June 6, 1978

[54] AUTOMATIC BLOOD ANALYZING SYSTEM

[75] Inventors: Robert Baxter, Jr., Stratford; Frank J. Antoci, Milford; William J. Tynes, III, Stamford; Pasquale M. Petrucci, Orange; George F. Martin, Westbrook, all of Conn.

[73] Assignee: J. T. Baker Chemical Co., Phillipsburg, N.J.

[21] Appl. No.: 681,285

[22] Filed: Apr. 28, 1976

[51] Int. Cl.² ........................................... G06M 11/00
[52] U.S. Cl. ........................... 235/92 PC; 235/92 CA; 235/92 R; 324/71 CP
[58] Field of Search .......... 235/92 PC, 92 CA, 151.3; 324/71 CP

[56] References Cited

U.S. PATENT DOCUMENTS

| 3,657,725 | 4/1972 | Estelle et al. | 235/92 PC |
| 3,868,498 | 2/1975 | Guggenbuhl | 235/151.3 |

Primary Examiner—Joseph M. Thesz
Attorney, Agent, or Firm—Weingarten, Maxham & Schurgin

[57] ABSTRACT

A system is provided for the automatic measurement of red and white blood cell counts and other blood parameters. The system includes hydraulic apparatus for the aspiration of a blood sample and the proper measurement of the parameters thereof. During operation, the system directs an operator at each step of the procedure, allowing only permitted functions to be performed, thereby decreasing the opportunity for operator error. Each blood cell count is performed twice and the answers compared, an indication of instrument malfunction being presented to the operator if the measurements do not agree within a predetermined percentage. The system monitors itself to detect malfunctions which may occur and alerts the operator to the occurrence of a malfunction.

23 Claims, 26 Drawing Figures

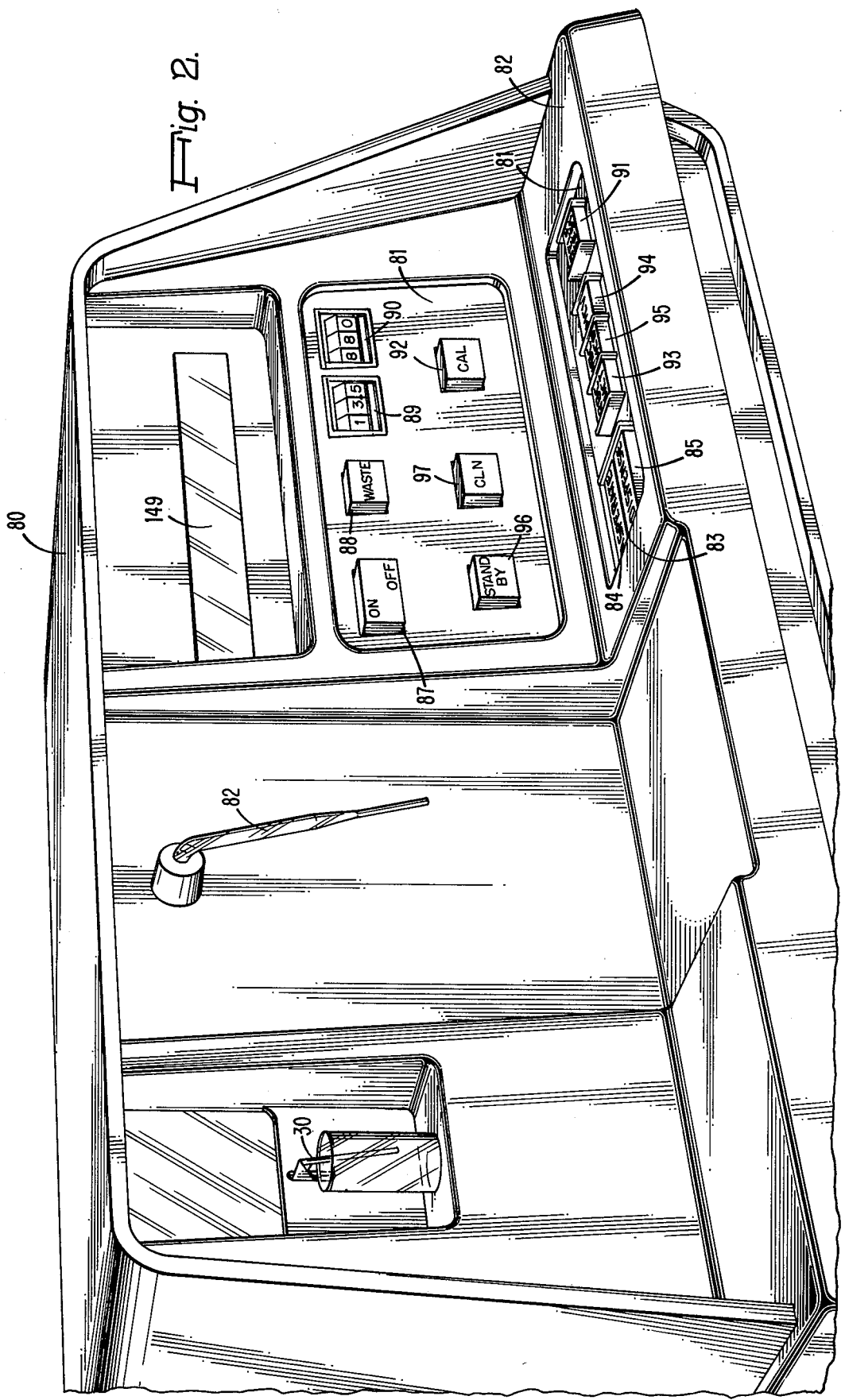

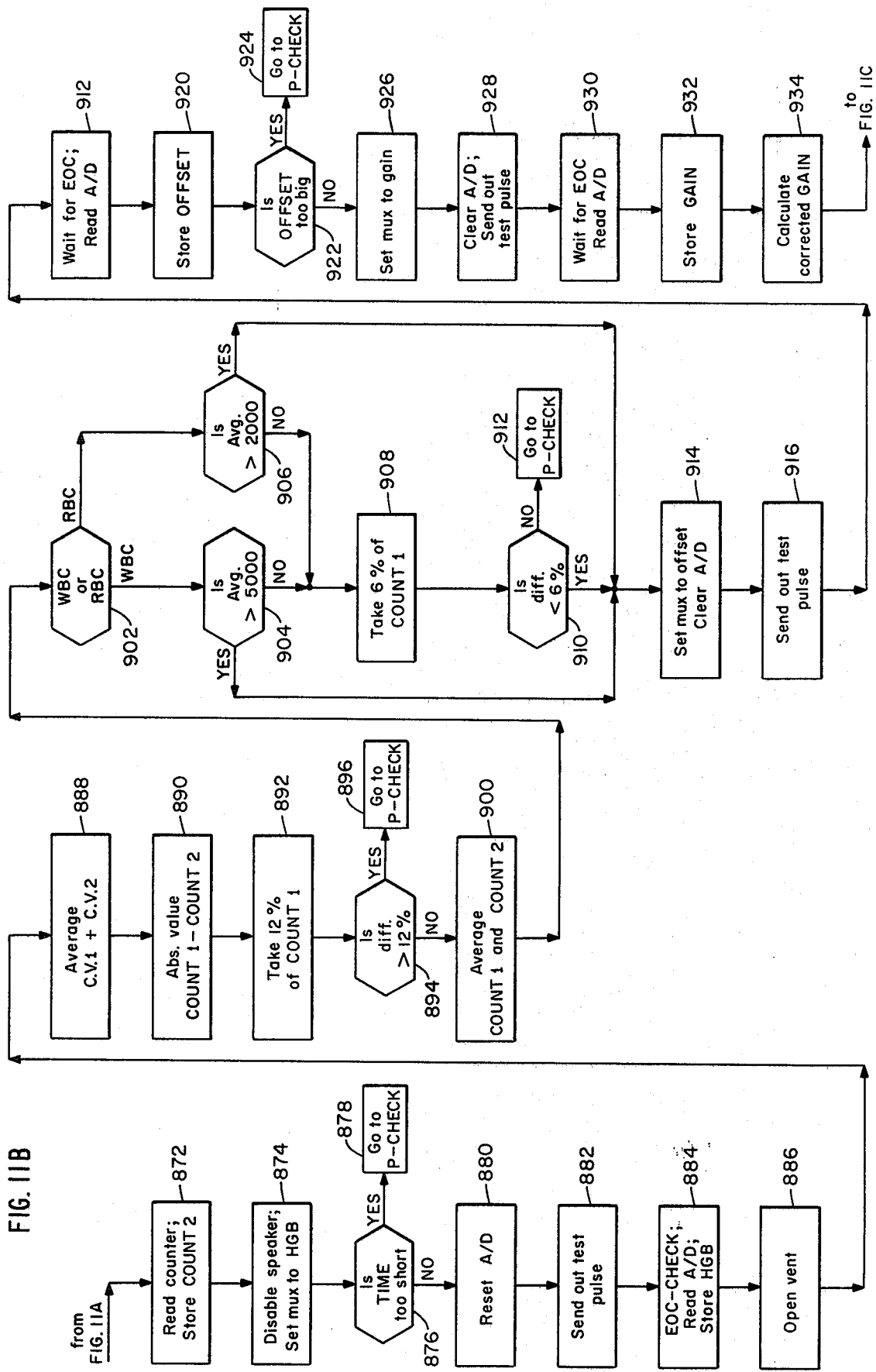

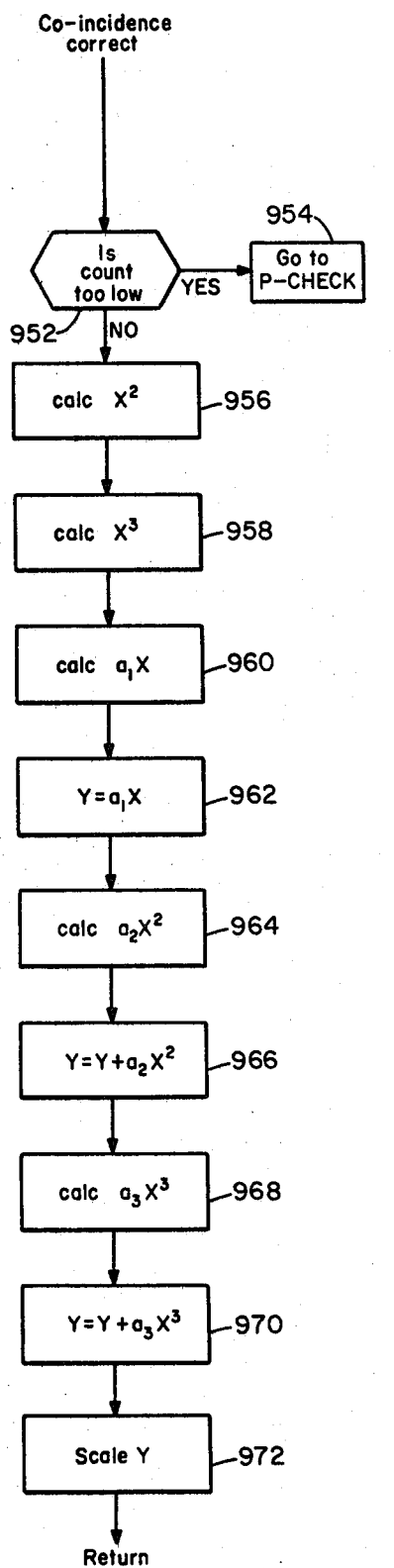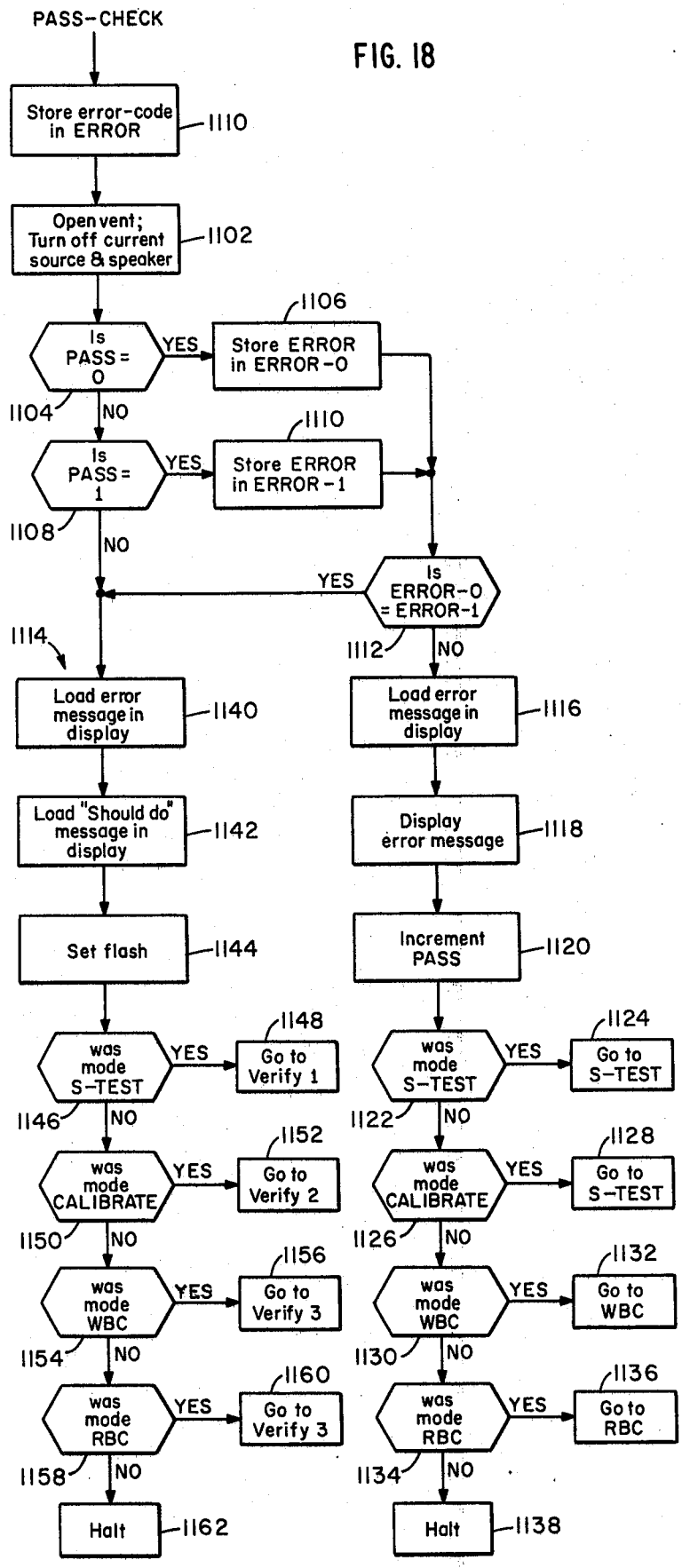
FIG. 12
FIG. 18

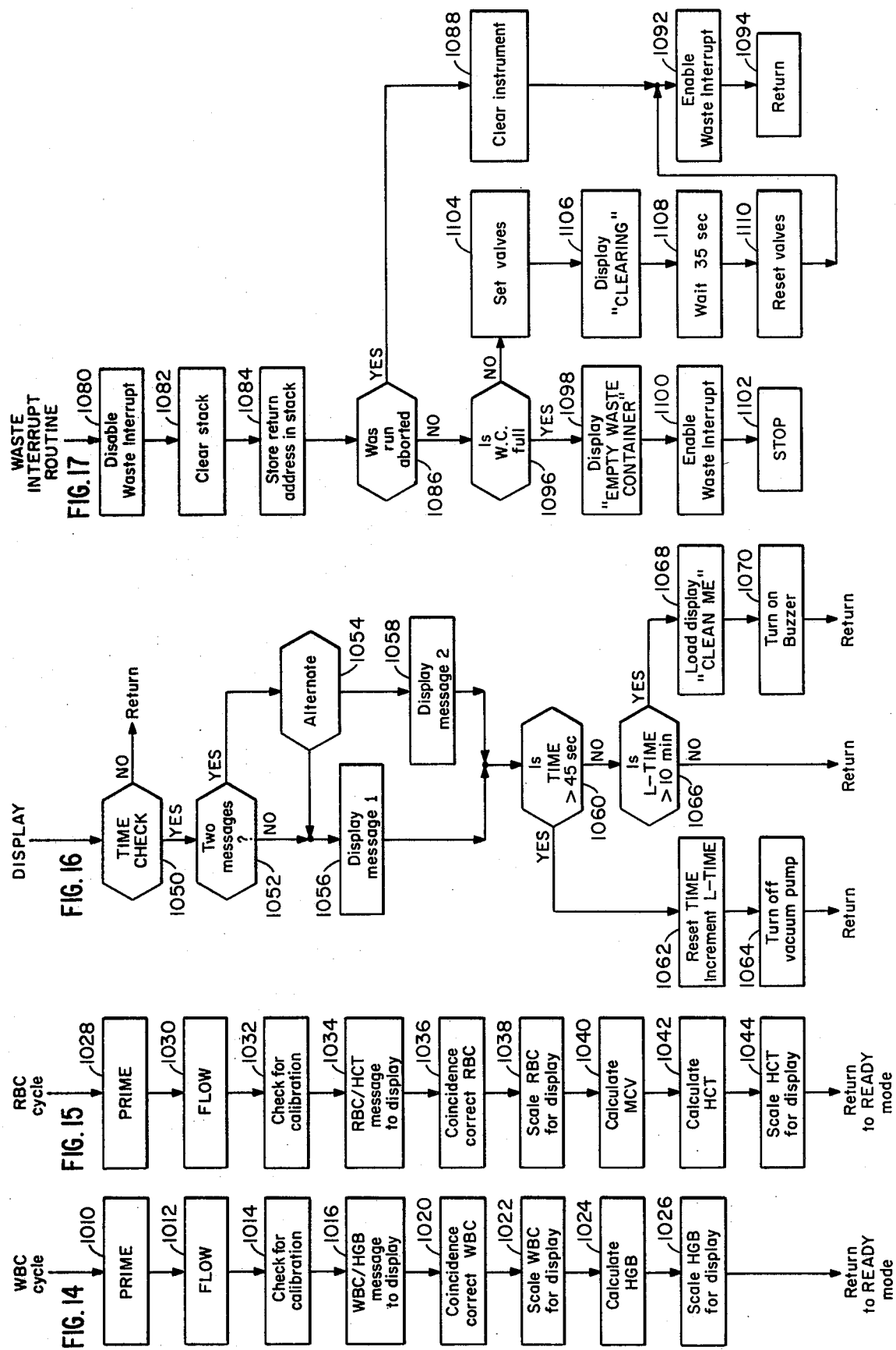

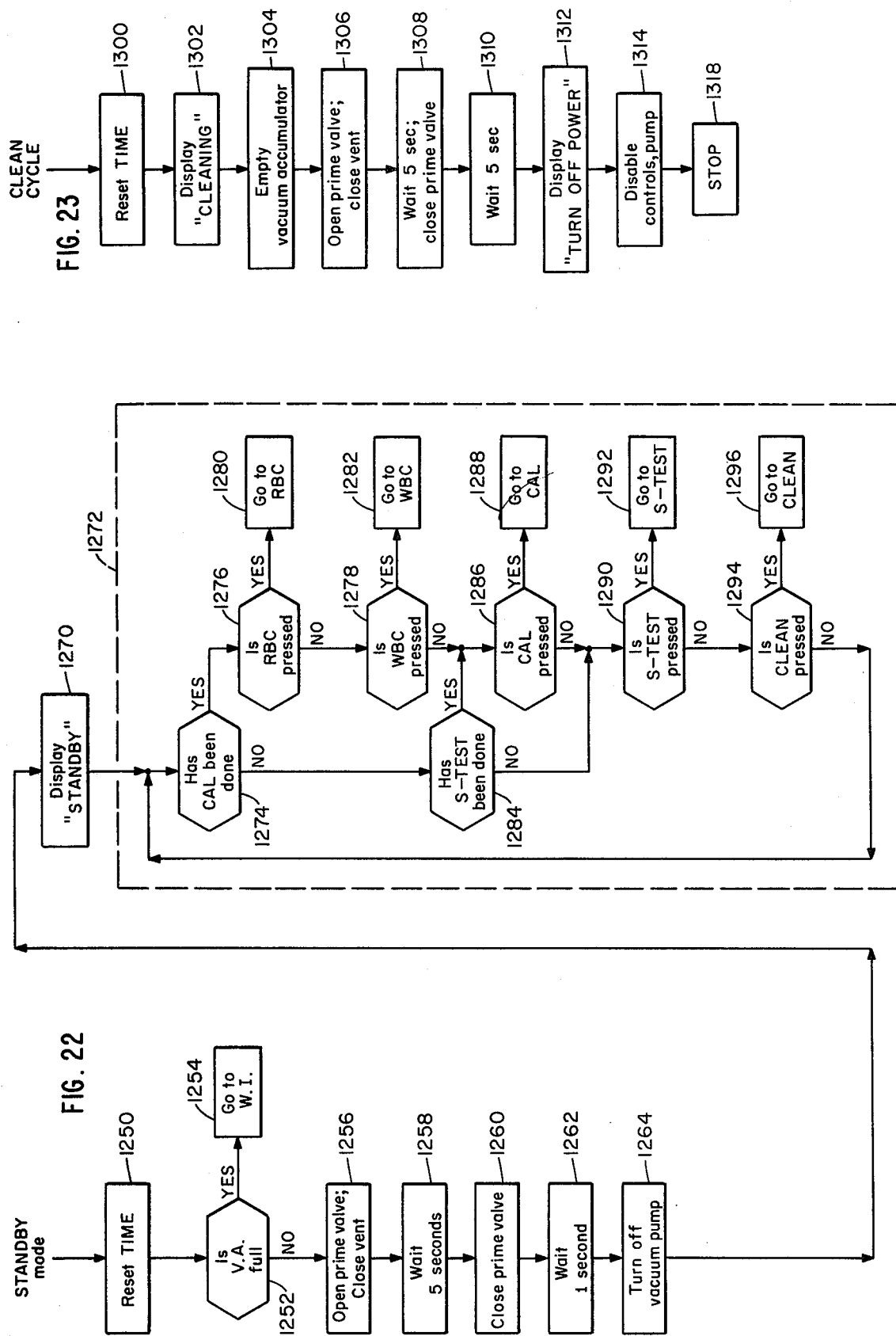

4,093,849

AUTOMATIC BLOOD ANALYZING SYSTEM

FIELD OF THE INVENTION

The present invention relates to particle counters, and more particularly to a system for the automatic measurement of blood cell counts and other blood parameters.

BACKGROUND OF THE INVENTION

Systems are known for the counting of red and white blood cells wherein a transducer is employed having a pair of electrodes disposed within a fluid path and with an aperture therebetween through which a blood sample is caused to flow. The impedance of the fluid path as sensed by the electrodes is materially altered by the presence of a blood cell within the aperture giving rise to electrical pulses which are electrically counted and which correspond to the number of blood cells passing through the aperture. Such systems employ means for metering a known volume of cell containing liquid, such that a cell count for a known volume of liquid can be provided. A preferred blood cell counting system is shown in U.S. Pat. No. 3,657,725, assigned to the assignee of this invention.

There is a need for blood cell counting systems which are automatic in operation so that relatively untrained personnel may be employed for system operation and so that less time is required for attendance to system operation even with trained personnel.

SUMMARY OF THE INVENTION

Briefly, the invention entails a system for performing automatic measurement of red blood cell counts, white blood cell counts, hematocrit, hemoglobin and mean cell volume. The system includes hydraulic apparatus for the aspiration of a diluted blood sample presented to the instrument by an operator, after which all further operations of a particular measurement cycle are carried out automatically by the instrument. During operation, the system directs the operator at each step of the procedure, allowing only permitted functions to be performed, thereby decreasing the opportunity for operator error. After initial startup of the instrument, the operator is directed to perform the required flush, self-test, and calibration procedures; and the instrument will not allow an operator to perform blood parameter measurements until these procedures have been successfully completed. During red and white blood cell counts, each count is performed twice and the answers compared. An indication of instrument malfunction is presented to the operator if the measurements do not agree within a predetermined percentage, otherwise the instrument displays the average of the two counts. The instrument continually monitors its operations to detect malfunctions. In the event a malfunction is detected, the instrument will notify the operator that such a malfunction has occurred and attempt to reperform the measurement. If the measurement can not be performed successfully, the instrument will cease operation and indicate proper remedial procedures to the operator.

DESCRIPTION OF THE DRAWINGS

The invention will be more fully understood from the following detailed description taken in conjunction with the accompanying drawings in which:

FIG. 2 is an elevation view of the front panel of the invention in a typical packaging configuration;

FIGS. 11A, 11B, and 11C are a flow diagram showing the steps carried out by the invention during a flow routine;

FIG. 12 is a flow diagram showing the steps carried out by the invention during a coincidence correction routine;

FIG. 14 is a flow diagram showing the steps carried out by the invention during a white blood cell count;

FIG. 15 is a flow diagram showing the steps carried out by the invention during a red blood cell count;

FIG. 16 is a flow diagram showing the steps carried out by the invention during a display routine;

FIG. 17 is a flow diagram showing the steps carried out by the invention during a waste interrupt routine;

FIG. 18 is a flow diagram showing the steps carried out by the invention during a pass-check routine;

FIG. 22 is a flow diagram showing the steps carried out by the invention during stand-by mode;

FIG. 23 is a flow diagram showing the steps carried out by the invention during a clean cycle.

DETAILED DESCRIPTION OF THE INVENTION

Figure 1:
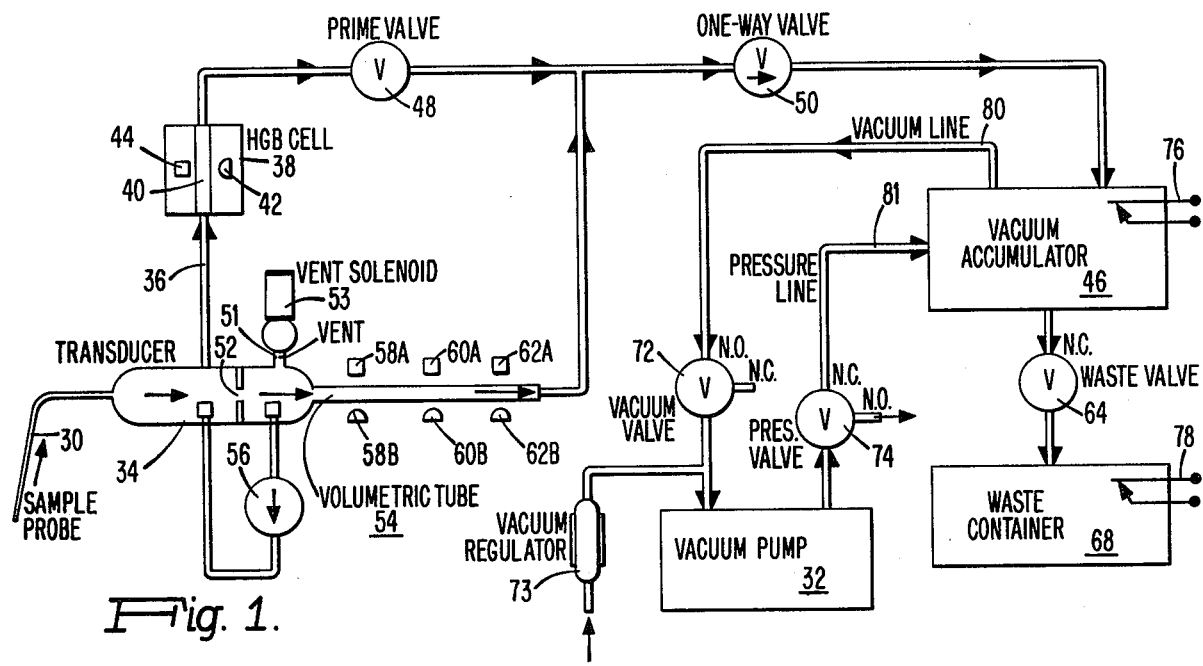
FIG. 1 is a diagram of the hydraulic apparatus of the present invention.

The hydraulic portion of the system by which a blood sample is drawn from a sample flask into the system and conveyed through the instrument for analysis is shown schematically in FIG. 1. To being operation, a flask containing a blood sample or other liquid to be drawn through the system is presented to sample probe 30. Sample probe 30 is immersed in the liquid which is aspirated through the probe and into the system by the action of a vacuum pump 32.

During normal operation of the instrument, vacuum pump 32 draws air from vacuum accumulator 46 through vacuum line 80 and vacuum valve 72. Vacuum regulator 73 serves to regulate the pressure created by vacuum pump 32, thereby tending to stabilize the vacuum in reservoir 46. Exhaust air from vacuum pump 32 is normally exhausted to the atmosphere through the normally open outlet of pressure valve 74.

The liquid flows through sample probe 30 into a transducer 34 from which the liquid may follow one of two paths, depending upon the test or function being performed by the system. The liquid may flow along a "prime path" from transducer 34 through tube 36 to HGB cell 38 wherein a hemoglobin, or HGB, measurement may be made. This measurement is photometrically done by passing the liquid from tube 36 through a flow-thru cell 40 which is illuminated by a light source 42. The light transmitted through tube 40 containing the liquid to be analyzed is detected by a photodetector 44 whose output is representative of the HGB measurement of the liquid being sampled. From HGB cell 38 the sample is drawn by the vacuum in vacuum accumulator 46 through a prime valve 48, a one-way valve 50, and into vacuum reservoir 46.

Alternatively, the liquid from sample probe 30 may be drawn by the vacuum in accumulator 46 through an orifice 52 in transducer 34 and thence through a volumetric tube 54 and one-way valve 50 into accumulator 46. Transducer 34 is a particle counter of a type well known to those in the art and commonly referred to as an impedance cell. In operation, a constant current source 56 causes a current conducted by the sample liquid within transducer 34 to flow through orifice 52. Particles in the sample liquid flowing through transducer 34 cause fluctuations in the voltage across orifice 52 as each of these particles flows therethrough. By monitoring this voltage, the number and size of particles flowing through the orifice can be determined.

Transducer 34 is coupled to volumetric tube 54 through which the sample liquid flows after passing through transducer 34, and in which the volume of the liquid flowing through transducer 34 and orifice 52 may be determined. Tube 54 is of glass or other suitable light transmissive material. Spaced along volumetric tube 54 are a first photodetector 58A and an associated light source 58B, a second photodetector 60A and associated light source 60B, and a third photodetector 62A and associated light source 62B. Each of these photodetector/light source pairs detects the passage of the liquid sample. Since the volume of volumetric tube 54 between each of the light source/photodetector paris is known, the volume of the sample liquid flowing through transducer 34 and orifice 52 may be precisely measured by monitoring the output of the photodetectors 58A, 60A and 62A. As will be further described below, the present system provides, during a single measurement run, two successive blood cell counts which are compared with one another, an output indication of the measured count being provided only when the successive counts are within a predetermined tolerance range.

After passage through volumetric tube 54, the sample is conveyed via one-way valve 50 to vacuum accumulator 46 and thence via a waste valve 64 to a waste container 68 external to the instrument. The accumulator 46 is coupled to the vacuum output of vacuum pump 70 by vacuum valve 32 and vacuum line 80. Vacuum regulator 73 serves to maintain the pressure in vacuum reservoir 46 constant to provide for a relatively constant flow speed of the sample liquid through the system. Accumulator 46 is coupled to the positive pressure output of vacuum pump 32 by pressure valve 74 and pressure line 81. The valves depicted in FIG. 1 have operating positions labeled as "Normally Open" (N.O.) and "Normally Closed" (N.C.), indicating the normal state of the valves during sample analysis. Vacuum reservoir 46 and waste container 68 each contain respective level sensing switches 76 and 78 which provide indications when the reservoir 46 or container 68 are full.

Referring to FIG. 2, there is shown the instrument as it would appear to an operator, including the display and front panel controls. Thus, the instrument is contained within a chassis 80 having a front panel portion 81 upon which are located the controls and displays of the instrument. Emerging from front panel 81 is sample probe 30 through which is aspirated the various solutions which flow through the machine during its different cycles.

Also emerging from front panel 81 is a second probe 82 coming from a diluter contained within the instrument. This diluter is used for properly diluting the blood samples to be analyzed and operates in the normal fashion. The diluter is controlled by front panel button 83. This button is divided into two separate individually lighted portions: a top portion 84 bearing the legend "ASPIRATE", and a bottom portion 85 bearing the legend "DISPENSE". Normally, when the diluter is ready to receive a blood sample to be diluted, top portion 84 of button 83 is lighted, indicating to the operator that the diluter is ready to aspirate a blood sample. The operator immerses diluter probe 82 into the blood sample and presses button 83. This causes the diluter to aspirate a precisely measured 80 microliter volume of the blood sample. When this has been done, the light illuminating the bottom portion 84 of button 83 will illuminate the "dispense" legend on button 83. After wiping the excess blood from diluter probe 82, the operator places a clean sample container beneath diluter probe 82 and presses button 83, causing the previously aspirated blood sample and 20 milliliters of diluant to be ejected into the sample container.

Front panel 81 also contains a display 149 on which are displayed to the operator the measured parameters of the sample being analyzed by the instrument. Display 149 also displays to the operator various messages during the operation of the instrument which inform the operator of the instrument's progress through a cycle, indicate the steps which the operator should next perform, and suggest appropriate remedial procedures in the event of an instrument malfunction. The exact nature of these messages and descriptions will become clearer as the operation of the instrument is more fully explained below.

Front panel 81 contains other controls for the instrument. Accordingly, there is located on front panel control an "ON/OFF" button 87 for initially applying power to the instrument. A "WASTE" button 88 is used by the operator in emptying vacuum accumulator 46, and to abort a sample run which is being carried out by the instrument, as described in more detail below in the description of the waste-interrupt cycle with reference to FIG. 17. Front panel thumbwheel switches 89 and 90 are used in properly calibrating the instrument before blood sample measurements are attempted. Accordingly, during a calibration run the known value of the hemoglobin, or HGB, measurement of the calibration sample is dialed into the instrument via front panel thumbwheel switches 89. Similarly, the known mean cell volume, or MCV, measurement of the calibration sample is entered into the instrument through thumbwheel switches 90.

The "SELF-TEST" button 91 may be pressed by the operator to initiate a self-test cycle, described in detail below. The "CAL" button 92 is pressed by the operator when he is ready to perform a calibration cycle prior to performing blood sample measurements.

The red blood count, or RBC, and hematocrit, or HCT, measurements are both made by the instrument during an RBC sample run. To begin an RBC sample run, the operator immerses sample probe 30 in a properly diluted sample and presses front panel "RBC/HCT" button 93. To display the mean cell volume, or MCV, measured during an RBC sample run, the operator presses front panel "MCV" button 94.

The white blood count, or WBC, and hemoglobin, or HGB, measurements are both made by the instrument during a WBC sample run. To initiate a WBC sample run, the operator immerses sample probe 30 in a properly diluted blood sample and presses front panel "WBC/HGB" button 95. To put the instrument in standby mode, the operator immerses sample probe 30 in deionized water and presses front panel "STBY" button 96. To perform a clean cycle, the operator immerses the sample probe 30 in cleaning solution and presses front panel "CLN" button 97.

The operation and interrelationship between the controls shown in FIG. 2 and the instrument hydraulics shown in FIG. 1, will become more apparent as the operation of the instrument is explained in detail below.

The normal operation of the instrument would proceed as follows. When the instrument is turned on, a warm-up cycle is commenced which lasts for approximately five minutes. This warmup cycle allows vacuum pressure, temperature, and other conditions within the instrument to stabilize before measurements are attempted. During the warm-up cycle, the instrument displays the message "FLUSH WITH WATER" on front panel display 149. To enable the instrument to proceed with the flush cycle, the operator places a beaker of deionized water underneath sample probe 30 and presses standby button 96. The instrument then aspirates the water which flows from transducer 34 through tube 36 and HGB cell 38 during a prime cycle.

To begin a prime cycle, vent solenoid 53 closes and prime valve 48 opens. This causes fluid to be aspirated through sample probe 30 into transducer 34. While prime valve 48 is open, fluid is drawn along the prime path from transducer 34 through line 36, HGB cell, prime valve 48, and one-way valve 50 into vacuum accumulator 46. During this period, some fluid is drawn through orifice 52 in transducer 34 by the vacuum in accumulator 46; however, orifice 52 is very tiny and offers a greater resistance to the fluid flow then does the fluid path through HGB cell 38. Thus, while prime valve 48 is open, most of the sample fluid flow is through HGB cell 38 and prime valve 48.

Six seconds after prime valve 48 opens, vent solenoid 53 opens, and one second later, prime valve 48 closes. When vent solenoid 53 opens, air flows through vent 51, orifice 52 and thence through the prime path. Transducer 34 is so constructed that the flow of air through vent 51 impinges upon orifice 52 and tends to clear any blockage which may have accumulated therein and helps keep orifice 52 clean. When prime valve 48 closes, air is drawn through volumetric tube 54 until vent solenoid 53 closes.

The water is then drawn through transducer 34, orifice 52, and volumetric tube 54 for approximately 45 seconds, flushing out the cleaning solution. During this period, the instrument displays the message "FLUSHING" on display 149. The flush cycle ensures that the cleaning solution has been completely eliminated from the instrument. If the flush cycle is completed before the warm-up period has ended, the instrument displays the message "WARMING-UP" until the warm-up period has ended.

After completion of the five-minute warm-up time, the message "RUN SELF-TEST" is displayed. To perform a self-test cycle, the operator places a beaker of diluant with a lysing agent under sample probe 30 and presses self-test button 91. The diluant is primed in during which time the message "PRIMING" is displayed. Upon completion of the prime cycle, the message "SELF-TEST IN PROGRESS" is displayed, and the self-test flow through transducer 34, orifice 52 and volumetric tube 54 is commenced. The instrument then performs the slef-test procedures described in detail below.

If the instrument has determined that it is operating properly during the self-test cycle, the message "RUN CAL TEST" is displayed. To perform a calibration cycle, the operator enters the MCV and HGB values of a calibration sample via front panel MCV and HGB thumbwheel switches 89 and 90. The operator then palces either the RBC or WBC sample under sample probe 30 and presses the CAL button 92. The message "CAL RBC OR WBC" is then displayed, and the operator presses the proper button corresponding to the sample placed under sample probe 30. The sample is primed in and the flow through volumetric tube 54 is begun. The appropriate message "RBC CAL IN PROGRESS" or "WBC CAL IN PROGRESS" is displayed, depending on which calibration is being done. During the calibration cycle, two counts are measured, the first count corresponding to the flow the the sample within volumetric tube 54 from detector 58A to detector 60A and the second count corresponding to the flow from detector 60A to detector 62A. The counts are compared and checked to see that they agree within a predetermined tolerance. The amplitude of the voltage pulses produced by the red blood cells as they pass through orifice 52 is proportional to the volume of the cells, and during RBC calibration, 3200 pulse heights are summed to produce the MCV value.

The measured MCV value is next compared with the value previously indicated to the instrument on thumbwheel switches 90 and the calibration factor for MCV is then calculated by the instrument. After the first calibration run has been carried out, the instrument will display "CAL RBC OR WBC" to instruct the operator to perform the remaining calibration run. During a WBC calibration run the output of HGB cell 38 is read, the measured HGB reading is compared with the value dialed in on thumbwheel switches 89, and calibration factor for the HGB reading is calculated.

At the completion of each calibration run, the count value and the corresponding calibrated value, HCT, or HGB, are displayed for ten seconds. Subsequently, the operator is instructed to run the other sample. When both WBC and RBC calibration runs have been successfully completed, the message "READY TO SAMPLE" is displayed, and the operator may proceed to test blood samples.

During operation the instrument periodically checks switch 76 in vacuum accumulator 46; and a waste interrupt cycle is initiated by the instrument when switch 76 in vacuum accumulator 46 detects that the accumulator 46 has become filled with fluid. Vacuum valve 72 is actuated, isolating vacuum line 80 from vacuum port of vacuum pump 32. Pressure valve 74 is also actuated, causing exhaust air from vacuum pump 32 which normally exhausts to the atmosphere to be directed through pressure line 81 to vacuum reservoir 46. Waste valve 64 opens, and the accumulated fluid in vacuum accumulator 46 is forced through valve 64 into waste container 68 by the air pressure from pressure line 81.

The machine will automatically alert an operator to indicate that a clean or standby cycle should be performed. After a sample has been processed, if no other operation is performed within approximately ten minutes, the instrument indicates to the operator by means of a buzzer that the machine should be put into clean or standby mode.

When a clean cycle is performed by the instrument, cleaning solution is presented to sample probe 30. The prime cycle is performed, after which cleaning solution is drawn through volumetric tube 54. After 5 seconds the vacuum pump is turned off and the display indicates that the instrument power should be turned off.

In standby mode, deionized water is presented to sample probe 30. A prime cycle is performed after which the water is drawn through volumetric tube 54. After one second, the vacuum pump is turned off, and display 149 indicates that the instrument is in standby mode.

Figure 3:
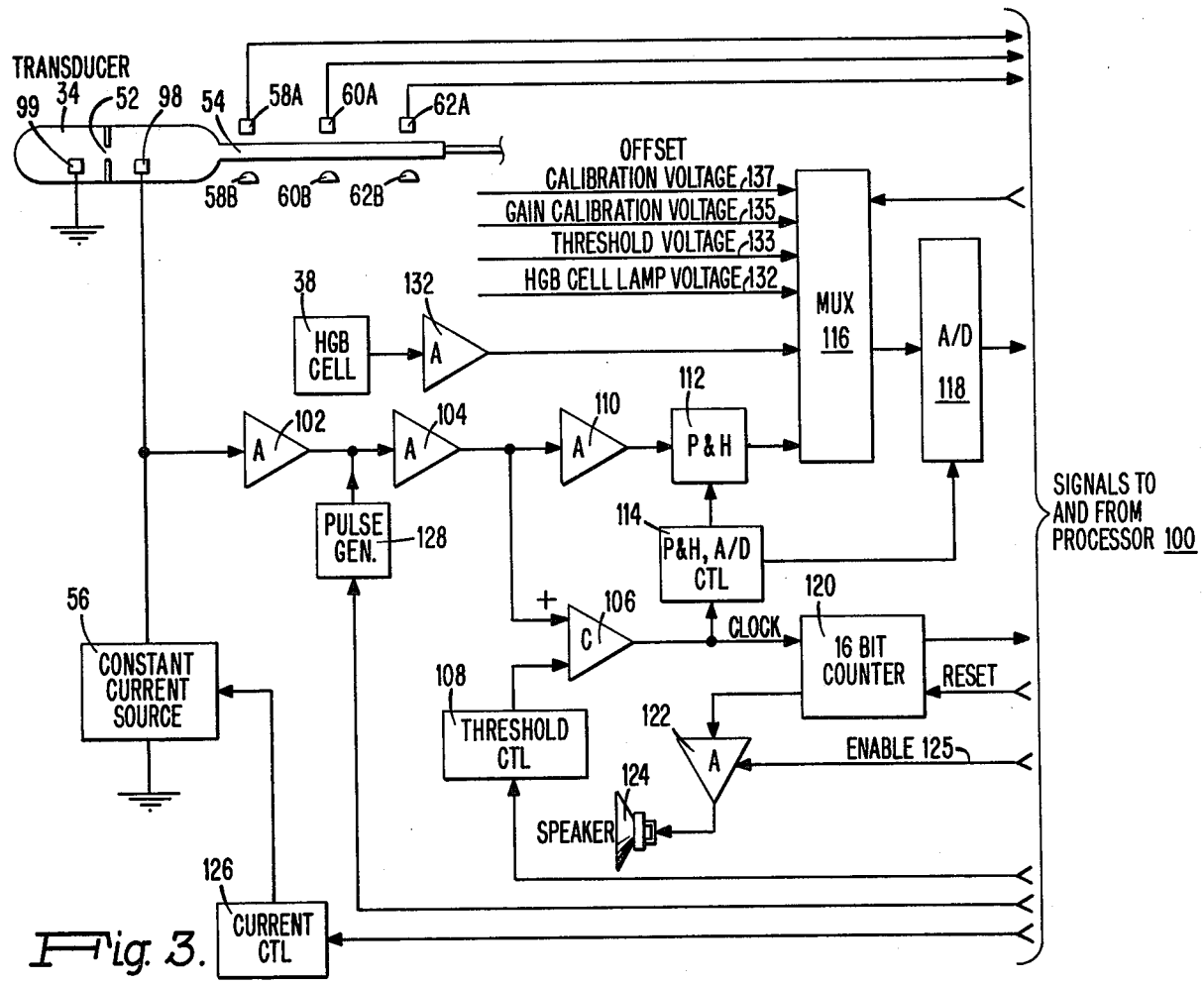
FIG. 3 is a schematic diagram of the measurement electronics of the invention.

FIG. 3 is a block diagram showing the analog electronic circuitry of the instrument. This circuitry is in general controlled by and sends signals representative of blood parameters to a processor 100 which is described in more detail below with reference to FIG. 4.

In operation, constant current source 56 causes a current, conducted by the sample liquid to flow between electrodes 98 and 99, which current flows through orifice 52 in transducer 34. As individual red or white blood cells contained in the sample pass through orifice 52, the resistance across the orifice and between the electrode changes, causing voltage fluctuations across electrodes 98 and 99. These voltage fluctuations are representative of both the number and the size of the blood cells passing through orifice 52.

The voltage fluctuations are amplified by amplifiers 102 and 104. The output of amplifier 104 is applied to one input of a comparator 106. When the voltage fluctuation exceeds a level determined by a threshold control 108, the output of comparator 106 changes state. This change in the state of the output of comparator 106 indicates the passage through orifice 52 of a red or white blood cell, depending on the measurement being taken.

The output of amplifier 104 is further amplified by amplifier 110 and applied to the input of a peak and hold circuit 112. When transducer 34 and the above-described circuitry detect the passage of a blood cell through orifice 52, the output of comparator 106 enables a control circuit 114. This control circuit 114 causes peak and hold circuit 112 to detect the peak amplitude of the voltage pulse which caused control circuit 114 to be enabled and which is applied to peak and hold circuit 112 by amplifier 110.

The output of peak and hold circuit 112 is applied through an A/D input multiplexer 116 to an A/D converter 118. The output of peak and hold circuit 112 corresponds to the maximum voltage across orifice 52 produced by the flow therethrough of a blood cell. Since the degree of blockage of orifice 52, and hence the voltage drop thereacross, is a function of the cell size, the output voltage from peak and hold circuit 112 is representative of the cell volume. Control circuit 114 starts the A/D conversion process after a peak has been detected and prevents peak and hold circuit 112 from being triggered until the A/D conversion has been completed and the digital value has been read by processor 100. A/D converter 118 converts the analog input from peak and hold circuit 112 and multiplexer 116 into binary form. This binary representation of the pulse height produced by the passage of a blood cell through transducer 34 is applied to processor 100.

The output from comparator 106 is also applied to the clock input of a 16-bit counter 120. Counter 120 counts the voltage pulses from transducer 34 whose amplitude exceeds the threshold set by threshold control 108, as determined by comparator 106. The parallel outputs of counter 120 are applied to processor 100, where they are read at appropriate times. Counter 120 may be reset to zero by a reset signal from processor 100. An intermediate bit is taken from counter 120 and applied to amplifier 122 which drives speaker 124. An enable signal from processor 100 is also applied to amplifier 122, allowing speaker 124 to be turned on and off. Speaker 124 provides an operator with an aural verification of the instrument operation while the instrument is analyzing a sample. An experienced operator also is able to quickly detect the occurrence of some types of malfunctions from the cadence emitted by speaker 124, for example, a blockage of orifice 52.

Constant current source 56 is controlled by a current control circuit 126. During times when particles are not being counted by transducer 34, signals from processor 100 cause constant current source 56 to be turned off by control circuit 126 to prevent the formation of electrolysis bubbles within the transducer.

Pulse generator 128 applies signals to the input of amplifier 104 which are used for test purposes when the instrument is in self-test mode, described in greater detail below. Pulse generator 128 is capable of providing pulses of two different amplitudes, a small amplitude and a relatively larger amplitude, in response to signals from processor 100.

The input to A/D converter 118 is selected by A/D multiplexer 116. Multiplexer 116 applies the appropriate input signal to be converted to A/D converter 118 in response to signals from processor 100. During red and white blood cell counts, the output of peak and hold circuit 112 is applied to converter 118 by multiplexer 116. During WBC runs, after the particle count has been measured, multiplexer 116 applies the output of HGB cell 38 and amplifier 132 to A/D converter 118 for conversion.

During self-test and calibration runs, the processor causes multiplexer 116 to apply a gain calibration voltage 135 to A/D converter 118. Gain calibration voltage 135 is a precisely controlled voltage of approximately ten-elevenths the full scale voltage of A/D converter 118. The output from A/D converter 118 in response to the precisely known gain calibration voltage 135 is used by processor 110 to calibrate the gain of A/D converter 118.

An offset calibration voltage 137 is also applied to A/D converter 118 by multiplexer 116 and processor 100 during calibration and sample runs. Offset calibration voltage 137 is a small, precisely-known voltage of approximately 100 millivolts. By applying this voltage to A/D converter 118 and reading the resulting digital output from the converter, processor 100 is able to determine the magnitude of both positive and negative offset errors which may exist in A/D converter 118.

The threshold voltage 133 from threshold control 108 and HGB cell lamp voltage 132 from the illumination source within HGB cell 38 are also applied to inputs of multiplexer 116. These voltages are not used during normal instrument operation, but are made available so that they can be converted and displayed by the instrument for recalibration thereof during certain maintenance procedures, such as replacing HGB cell 38 or replacing the analog circuit board of which threshold control 108 is a part.

The outputs from photodetectors 58A, 60A and 62A are applied to processor 100. While particle counts are being carried out by the instrument, these inputs are monitored to accurately measure the volume of the sample for which the particle count is being done. The time which it takes for the sample to flow between the photodetectors is also checked to determine any abnormal conditions.

Figure 4:
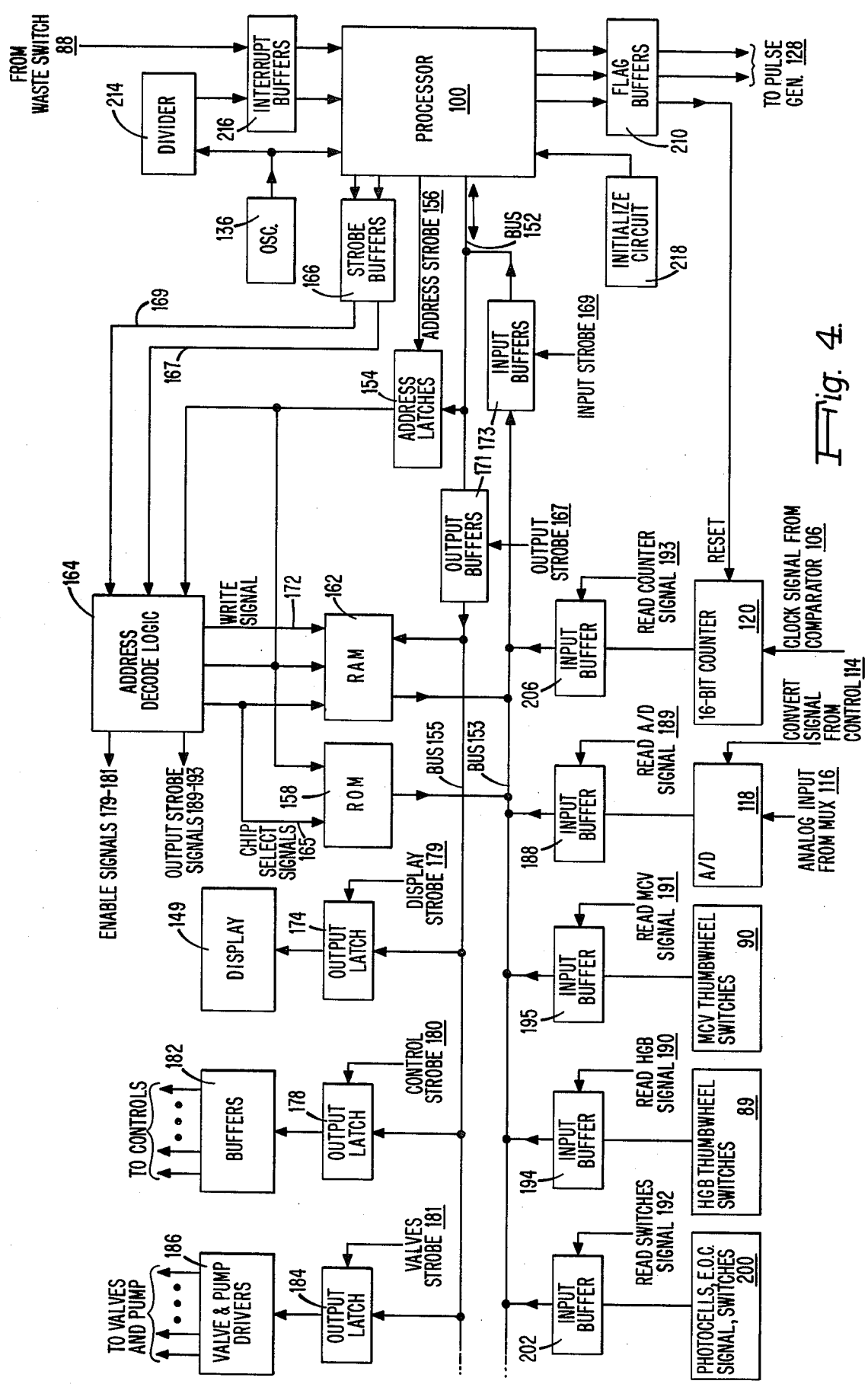
FIG. 4 is a schematic diagram showing the interconnection of the processor with the other elements of the invention.

Referring to FIG. 4, the means by which processor 100 controls the operation of the instrument is explained. The functions or processor 100 may be performed by many different types of digital data processing equipment, including microprocessors. Many microprocessors are commercially available which may be used in implementing the invention, and the general principles associated with the implementation and operation of these microprocessors are well known to those in the art. One microprocessor suitable for use with the present invention is the National Semiconductor 16-bit Pace microprocessor. This microprocessor is used in the preferred embodiment described. The Pace microprocessor is well known and widely available, and extensive documentation of its structure and operation has been published. For this reason, the detailed operation and structure of processor 100 need not be further elaborated upon hereinbelow. Other digital processors and microprocessors may be suitable for use with the present invention, and the implementation of the present invention with a processor other than that described will be readily apparent to one of ordinary skill in the art. Accordingly, the description of a particular microprocessor in connection with the preferred embodiment is not to be construed as a limitation upon the invention.

The principal means by which processor 100 communicates with the remainder of the system is via input-/output/address bus 152. Bus 152 is typically a 16-bit parallel digital bus, and serves to convey input data to processor 100, output data from processor 100, and address information from processor 100. Each of these different types of information is present on bus 152 during different times, as indicated by additional signals from processor 100. This operation will become more apparent as the operation of processor 100 is further explained.

The address data from processor 100 indicates the device with which it will communicate and is applied to bus 152 at a particular period in the operation of the processor. This address information is strobed into address latches 154 by an address strobe signal 154 from processor 100. Thereafter, the address information is removed from bus 152 to allow data from processor 100 or data being entered into processor 100 to be put on bus 152.

The address information stored in address latches 152 is applied to read-only memory 158, random access memory 160, and address decode logic 162. Process 100 also generates an input data strobe signal for clocking data into the processor, and an output data strobe, for clocking data from the processor. These strobe signals are applied to strobe buffers 166 and thence to address decode logic 164.

In response to the address data from address latches 154, and the input strobe signal 169 and output strobe signal 167 from strobe buffers 166, address decode logic produces the following signals. First, address decode logic produces several read enable signals 179 – 181, described in detail below, which are used to apply information from the switches and measurement circuitry of the instrument to bus 152 at the proper time so that this information may be read by processor 100. Second, address decode logic 164 produces output strobe signals 189 – 193, described in greater detail below, which are used to strobe data applied to bus 152 by processor 100 into output latches where this output data is held for use by other parts of the instrument. Third, address decode logic produces a write signal 172 which is applied to random access memory 162 to store data from processor 100 therein at the appropriate times. Fourth, address decode logic produces chip select signals 165 which are used to enable the proper read-only memory and random access memory chips at the proper time.

Input/output/address bus 152 is split into an input bus 153 and an output bus 155 by input buffers 173 and output buffers 171, respectively. These buffers are strobed at the proper times by input and output strobe signals 169 and 167 from strobe buffer 166. The output stages of input buffers 173 are in a high-impedance state when not enabled by input strobe 169. Read-only memory 158 is typically comprised of approximately 3K 16-bit words. This data contains digital instructions which cause processor 100 to perform the proper steps in controlling the instrument. Appended to the present application is a typical listing of the contents of read-only memory 158 for use in controlling the instrument as described hereinbelow. This set of instructions is particularly adapted for use with the above-described Pace microprocessor.

In response to the proper signals from address latches 154, read-only memory 158 applies digital data to bus 152. Typically, read-only memory 158 contains output stages which present a high impedance to bus 152 when-read only memory 158 is not enabled by chip select signals 165. This obviates the need for buffers between read-only memory 158 and bus 152.

Random access memory 162 serves to store the different variables and parameters needed for the operation of processor 100. Random access memory 162 typically contains approximately 256 16-bit words. In "read mode", the appropriate address data is applied to random access memory 162 by address latches 154, causing the data stored in the selected location of random access memory 162 to be applied to bus 152. Typically, random access memory 162 contains output stages similar to those of read-only memory 158 which present a high impedance to bus 152 when not enabled by chip select signals 165. In "write mode", the address of the location in random access memory 162 in which data is to be stored is strobed into address latches 154. The data to be stored is then applied to bus 152 by processor 100. In response to the address signals from address latches 154 and the data output strobe signal from processor 100 and strobe buffers 166, address decode logic produces write signal 172 which stores data on bus 152 into random access memory 162.

Processor 100 produces output signals which control display 149, the hydraulics, and the measurement electronics of the instrument in the following manner. First, an address signal representative of the function or functions to be controlled is applied to bus 152 and then stored in address latches 154 by address strobe 156. Next, processor 100 applies the appropriate data to bus 152. While this data is present on bus 152, the data output strobe signal is applied to strobe buffers 156 and thence to address decode logic 164. In response to the data output strobe and the address signals designating the particular function being controlled, an address decode logic 164 produces the appropriate output strobe signal which clocks the data present on bus 152 into an output latch where it is retained for utilization by the instrument.

Accordingly, data is transferred to display 149 from processor 100 in the manner described above. Data applied to bus 152 by processor 100 is clocked into output latch 174 by display strobe signal 179 from address decode logic 164. In this manner, processor 100 displays to the operator measured blood parameters and instructions regarding the proper operation of the instrument.

Similarly, control information is strobed from processor 100 into output latch 178 by a control strobe signal 189 from address decode logic 164. The data stored in latch 178 is applied via buffers 182 to control multiplexer 116, threshold control circuit 108, speaker enable input 125, current control 126, and a buzzer which is used to attract the operator's attention. It should be noted that processor 100 controls all of the above functions with one output word.

The hydraulics of the instrument are controlled by data from processor 100 which is clocked into an output latch 184 by valve strobe signal 181. The data in output latch 184 is amplified and buffered by valve and pump drivers 186 and controls vacuum pump 32, prime valve 48, vent solenoid 53, waste valve 64, vacuum valve 72, and pressure valve 74.

To read data from the various switches and measurement circuits within the instrument, processor 100 first clocks the appropriate address into address latches 154. Next, processor 100 monitors bus 152 while the data input strobe signal is applied to address decode logic 164 via strobe buffers 166. Address decode logic 164 then produces the appropriate read enable signal 189 – 193 which causes an input buffer to apply the selected data to bus 152, and this data is read by processor 100. Typically, the input buffers are of the type which present a high impedance to bus 152 when they are not enabled.

Accordingly, the output of A/D converter 118 is applied to bus 152 via input buffer 188 in response to read A/D signal 189 produced by address decode logic 164. Similarly, processor 100 reads calibration data from front panel HGB thumbwheel switches 89 and MCV thumbwheel switches 90 via input buffers 194 and 195 in response to the appropriate read HGB signal 190 and read MCV signal 191 from address decode logic 164.

The processor reads the signals 200 from the photocells, the EOC signal from A/D converter 118, and signals from the remaining switches concurrently, and these signals are applied to bus 152 via input buffer 202 in response to read switches signal 192 from address decode logic 164. The signals which are read include: signals from the front panel switches including self-test switch 91, claibrate switch 92, RBC switch 93, MCV switch 94, WBC switch 95, standby switch 96, and clean switch 97; the output from switch 76 in vacuum accumulator 46 and switch 78 in waste container 68 indicating that the corresponding container is full; the outputs from photodetectors 58A, 60A, and 62A; and the EOC signal from A/D converter 118.

Counter 120 is read by processor 100 in the same manner, with the output from counter 120 being applied to bus 152 via input buffer 206 in response to read counter signal 193 from address decode logic 164. Processor 100 resets counter 120 by setting and resetting an appropriate flag. This flag output from processor 100 is applied to flag buffer 210 and thence to counter 120 providing the reset signal therefor. Two other flag outputs from processor 100 are applied via flag buffers 210 to pulse generator 128. These two flag outputs are used by processor 100 to produce the large test pulses and small test pulses from pulse generator 128.

The output from an oscillator 136 is applied to the clock input of processor 100 to provide the clock signals therefor. The output from oscillator 136 is also applied to divider 214. Oscillator 136 typically has a clock frequency of approximately 2 MHz., and divider 214 reduces this clock frequency to approximately 100 Hz. The output from 214 is applied to interrupt buffers 216 and thence to an interrupt input to processor 100 to provide a real time clock capability as described below. The output from waste switch 88 is also applied via input buffers 216 to an interrupt input to processor 100.

Initialize circuit 218 detects when power is initially applied to the instrument and causes processor 100 to properly begin operation.

Figure 5:
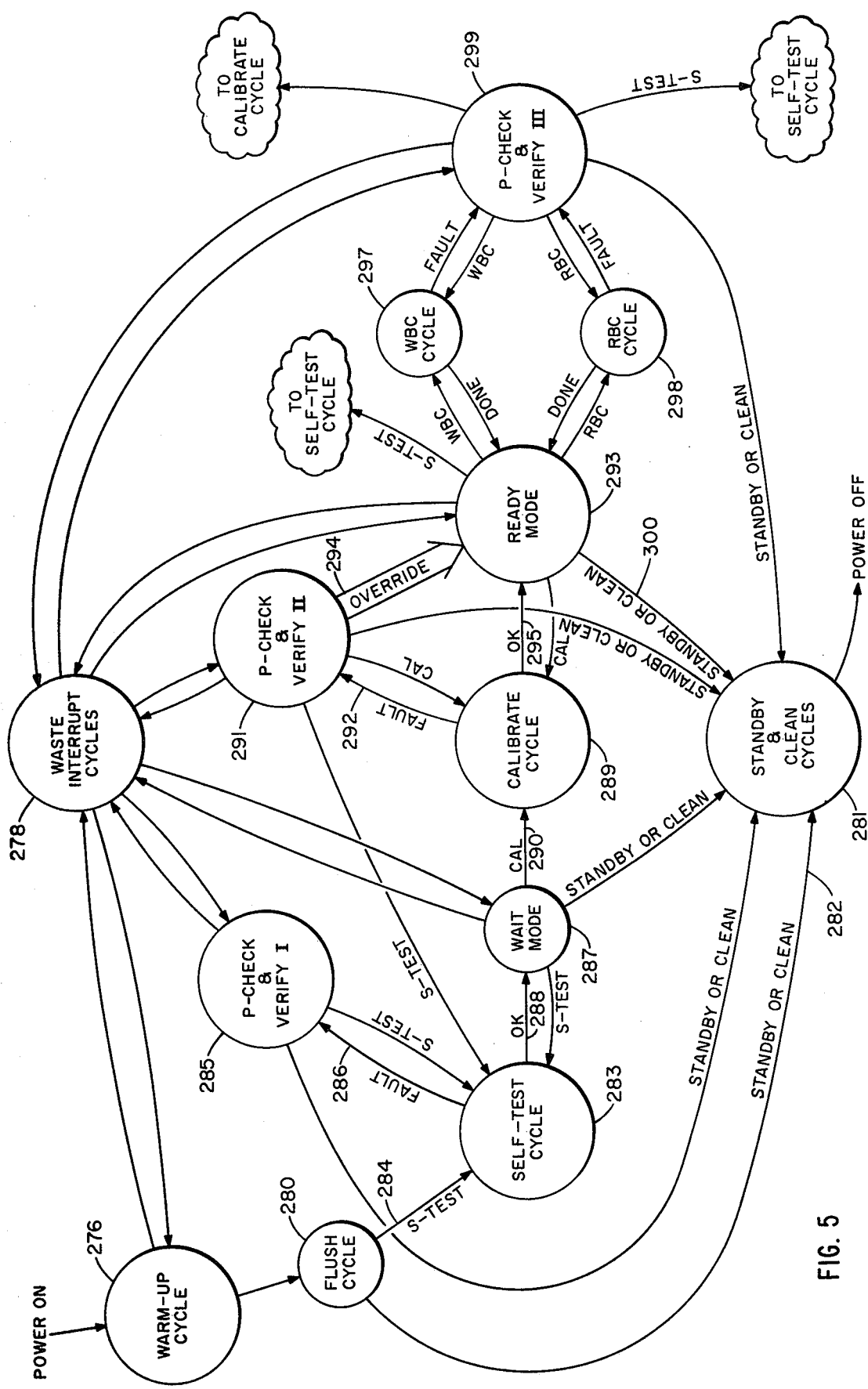
FIG. 5 is a state diagram showing the various different states of the system and permitted paths therebetween.

FIG. 5 is a state diagram showing the paths by which the instrument is permitted to proceed between the different cycles and modes which compose the procedures by which it performs its functions. The steps carried out in performing each of these individual cycles and modes are described in greater detail below with reference to the flow diagrams of FIGS. 6 through 23. At this time, however, it will be helpful to briefly describe the different states which the instrument passes through in performing its functions. The interrelation of these different states will become clearer as each is described in greater detail below, and during these detailed descriptions, it may prove helpful to refer back to FIG. 5.

When power is first applied to the instrument, the instrument begins a warm-up cycle 276. If during this cycle the instrument detects that vacuum accumulator 46 is full, the instrument proceeds to waste interrupt routine 278, and after the appropriate receptacle is emptied, returns to warm-up cycle 276. During or after warm-up cycle 276, the instrument proceeds to perform a flush cycle 280 wherein the hydraulics of the system are flushed with water.

From flush cycle 280. the operation may instruct the machine to proceed to standby mode or to carry out a clean cycle in preparation for shutting off the instrument. This is done by pressing the appropriate button which will cause the instrument to proceed from the flush cycle 280 to the appropriate standby mode or clean cycle 281 as shown by path 282.

Normally, the operator will press the self-test button, and the instrument will proceed from flush cycle 280 to self-test cycle 283, as shown by path 284. The instrument then performs the selftest functions. If, in carrying out these functions, the instrument detects a fault or malfunction, the instrument will proceed to pass-check and verify I routine 285 as shown by path 286.

The pass-check and verify routines operate as follows. When the instrument detects a fault in carrying out a cycle, it branches to the appropriate pass-check routine. The pass-check routine displays a message to the operator, alerting the operator of a particular malfunction that has occurred. The pass-check routine will then automatically return to the cycle which the machine was performing when the malfunction occurred. The cycle is then repeated. If the cycle is performed by the instrument without a malfunction on the second attempt, the instrument proceeds in the usual manner thereafter. However, if a malfunction occurs on the second attempt to perform a cycle, the instrument will again branch to the appropriate pass-check routine.

After a second unsuccessful attempt, the pass-check routine causes the instrument to inform the operator of the particular malfunction which occurred. Following this message, the instrument then displays a message suggesting to the operator the appropriate corrective steps to be performed. The instrument then enters the appropriate verify routine where it waits for the operator to perform the proper corrective action. The operator then presses a front panel button corresponding with a machine cycle to which the instrument is permitted to proceed from that particular verify routine, and the instrument attempts to resume operation.

The verify I routine differs from the other pass-check and verify routines in that a self-test cycle will be attempted three times before the instrument gives up, unless the same malfunction occurs on both the first and second attempts. From the verify I routine 285, the operator is allowed to proceed to the standby, clean, and waste interrupt and self-test modes.

If the self-test cycle 283 is successfully completed, the instrument will proceed to wait mode 287, as shown by path 288. From wait mode 287, the operator may cause the instrument to go to the waste interrupt, self-test, standby, calibrate or clean cycles by pressing the appropriate buttons, as shown in FIG. 5.

Normally, an operator selects the calibrate cycle 289, as shown by path 290. If a malfunction or fault is detected during the calibrate cycle 289, the instrument will go to pass-check and verify II routine 291, as shown by path 292. If the instrument calibration fails on the second attempt, the verify II routine allows the operator to select the waste interrupt, self-test, standby, calibrate, or clean cycles. Additionally, an operator may elect to bypass the calibration and proceed to ready state 293 as shown by path 294. This would be done by an operator if it were only desired to perform a cell count in the WBC or RBC cycles. The proper operation of those parts of the instrument necessary to perform cell counts is verified in self-test cycle 283. Calibrate cycle 289 only calibrates variables necessary to measure the HGB, HCT, and MCV values of a sample. If the operator directs the machine to perform a cell count before a calibration cycle has been successfully completed, as shown by path 294, those blood parameters other than WBC and RBC are not displayed by the instrument.

If the calibration cycle is successfully completed, the instrument will proceed to ready mode 293, as shown by path 295. From ready mode 293, the operator may cause the instrument to branch to any of the other cycles by pressing the appropriate button. Normally, an operator will either press the WBC or RBC button to perform a sample run. The instrument will then proceed to the appropriate WBC cycle 297 or RBC cycle 298 and return to ready mode 293 when WBC or RBC measurements have been completed. If a malfunction or fault is detected by the instrument during a WBC or RBC sample run, the instrument branches to pass-check and verify III routine 299.

When the operator is finished performing blood samples, the standby or clean buttons are pressed to put the instrument in standby mode or to cause the instrument to perform a clean cycle in preparation to turning off. This causes the instrument to proceed from ready mode 293 to the standby or clean cycle 281, as shown by path 300. After a clean cycle has been completed, the operator turns off power to the instrument.

Figure 6:
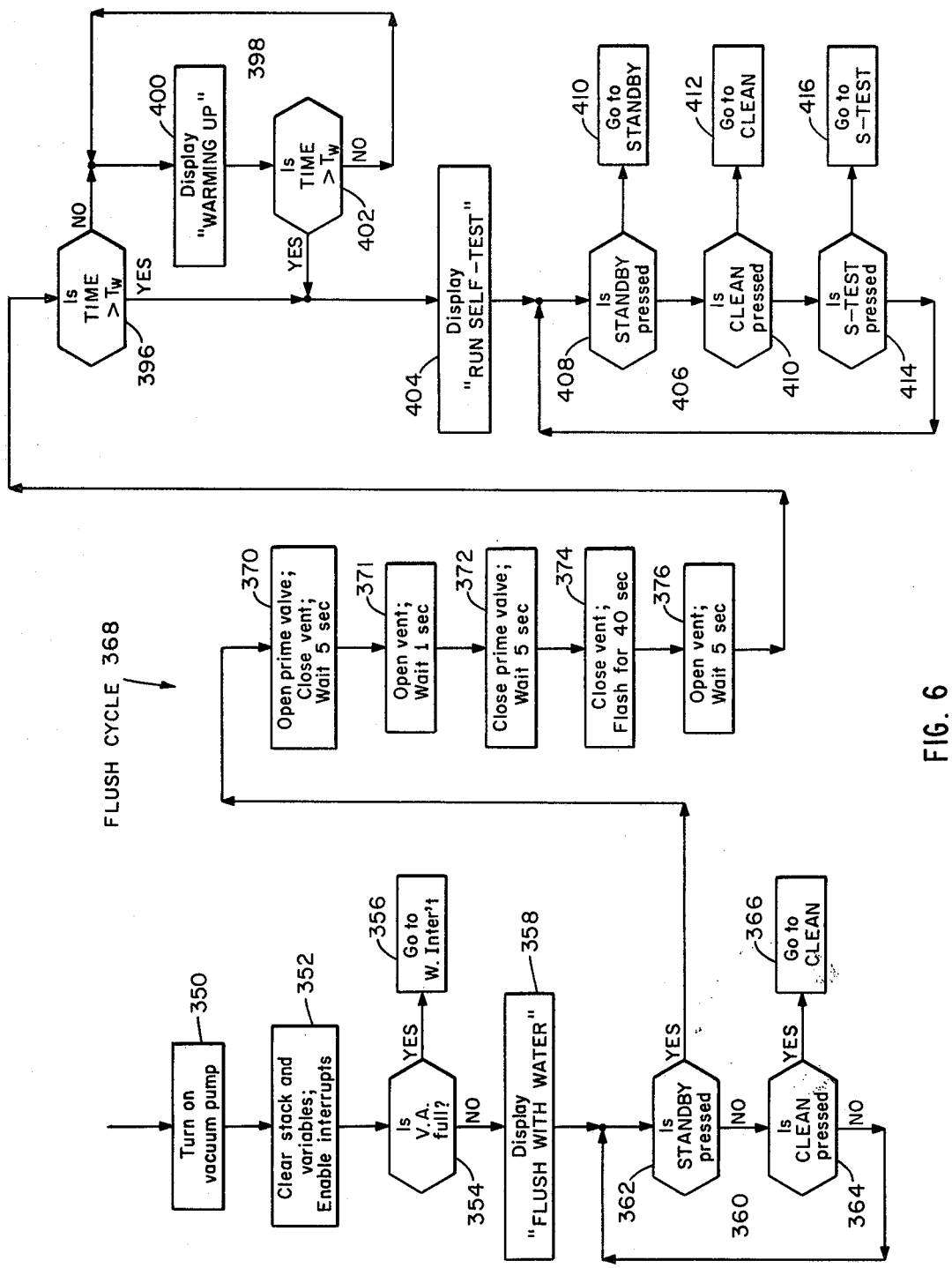
FIG. 6 is a flow diagram showing the steps performed by the invention during flush and warmup cycles.
Figure 7A:
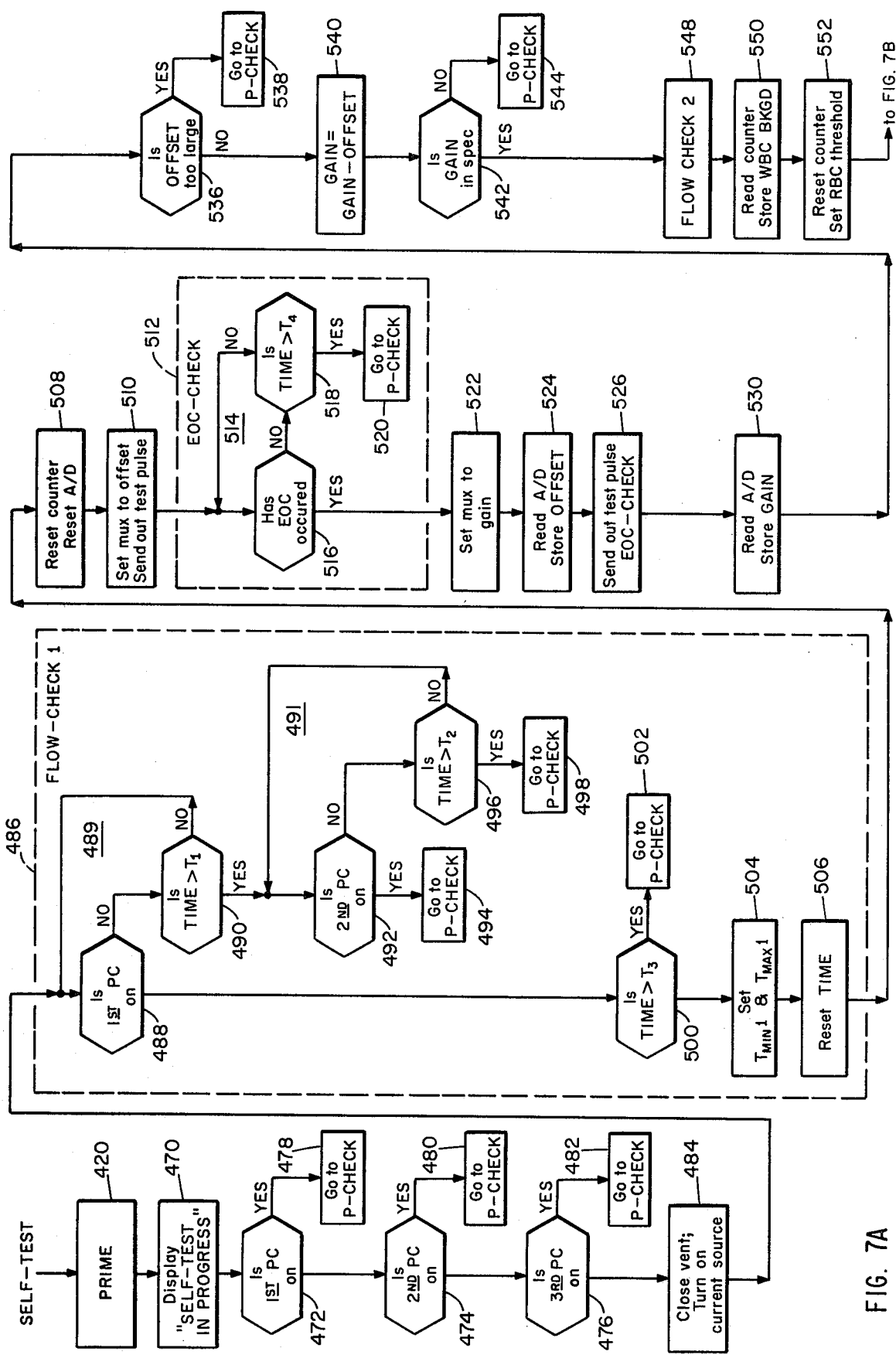
FIGS. 7A and 7B are a flow diagram showing the steps performed by the invention during a self-test cycle.
Figure 7B:
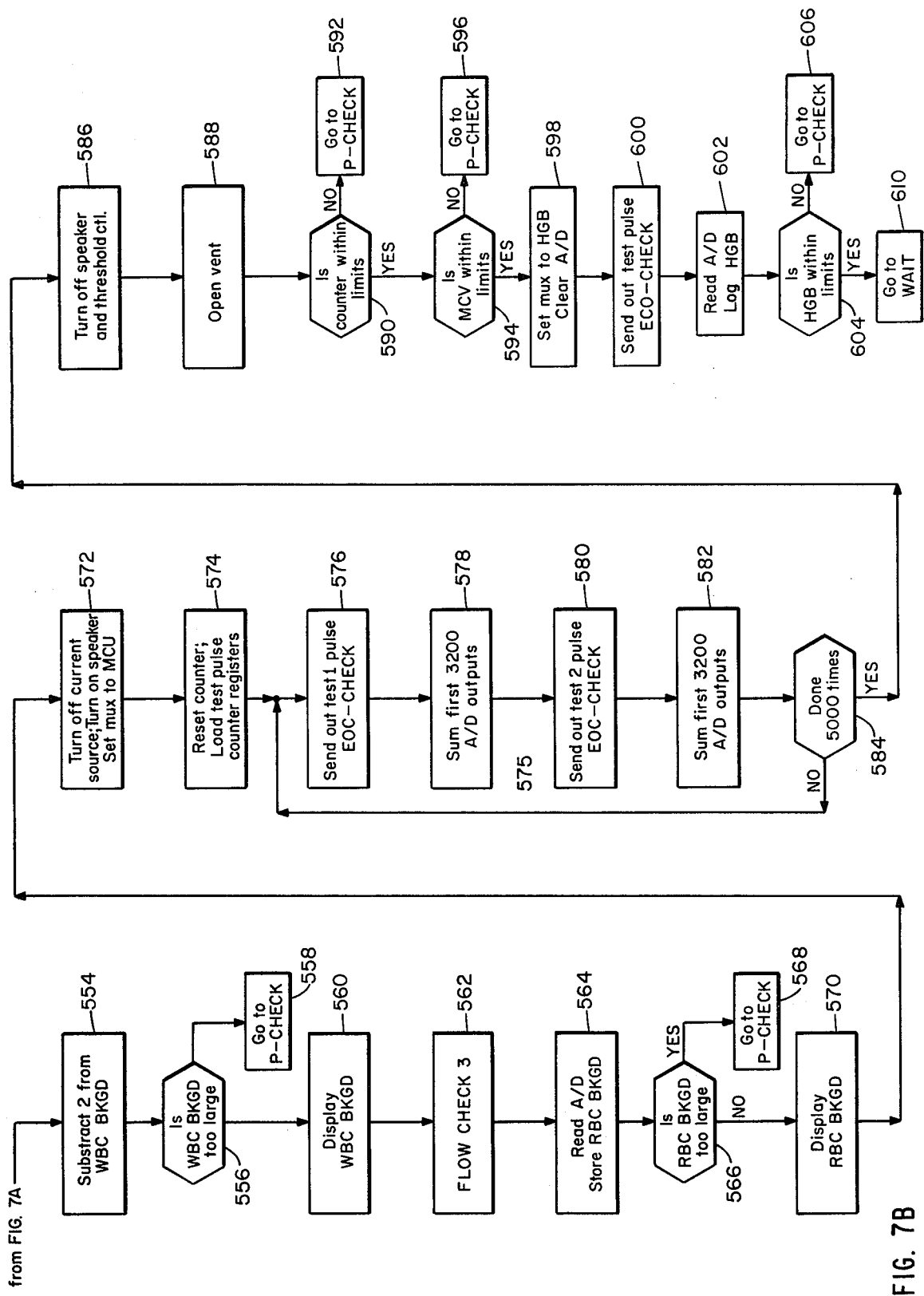

FIG. 6 is a detailed flow diagram of the steps performed by processor 100 during the warm-up and flush cycles. Immediately after the instrument is turned on, the processor causes the vacuum pump to be turned on, block 350. The stack and other operating variables within the processor are cleared, and the processor interrupt inputs are enabled, block 352. Next, the processor checks switches 76 and 78 to ascertain that the vacuum accumulator 46 is not full, block 354.

If the processor determines the container is full, the program skips to the waste interrupt sub-routine described below, block 356. Otherwise, the processor causes display 149 to display "FLUSH WITH WATER", block 358. The processor then enters loop 360 until the operator presses a permitted button. Loop 360 repeatedly checks the STANDBY button, block 362, and the CLEAN button, block 364, to determine if either has been pressed. The pressing of any other button by the operator is ignored by the processor, thereby preventing an inexperienced or careless operator from inadvertently skipping the following necessary operations for correct start-up of the instrument.

If at this point the operator wishes to turn off the machine, CLEAN button 97 is pressed and the processor will jump to the clean sub-routine described below in preparation for turning off the machine, block 366. Normally, the operator will place a beaker of water under sample probe 30 and press the STANDBY button 96, and the processor will proceed to carry out the steps of flush cycle 368.

The instrument begins the flush cycle by opening prime valve 48 and closing vent 51, block 373. This causes deionized water to be aspirated through sample probe 30 and along the prime path through HGB cell 38. After five seconds, vent 51 is opened, causing air to be drawn in through vent 51, through orifice 52, after which it bubbles through the prime path, drawn by the vacuum in vacuum accumulator 46, block 372. This reverse flow of air through orifice 52 causes any debris which may have lodged therein to be removed. After one second, prime valve 48 is closed, block 372. Five seconds later, vent 51 is closed, causing the deionized water to be drawn through transducer 34, orifice 52, and volumetric tube 54, block 374. This is continued for 40 seconds, flushing the system. After 40 seconds, vent 51 is again opened, allowing air to be drawn through volumetric tube 54, and this is continued for five seconds before the instrument proceeds further, block 376.

Oscillator 136 applies clock pulses to processor 100 at regular intervals of ten milliseconds. These clock pulses are applied to a real time interrupt input of the processor. Each time this interrupt signal occurs, the processor increments a variable denoted as TIME by the appropriate amount, after which the processor returns to the function which it was previously performing. Thus, the TIME variable serves as a real time clock for processor 100 which is accessible by all routines carried out by the processor. In this manner, timing of operations during sample tests may be accomplished. Additionally, when the instrument is in an inactive state, the TIME register is repeatedly checked. If no operation is performed by the instrument within a predetermined time, the instrument will indicate that if should be put in standby mode or clean mode. This prevents instrument malfunctions which may be produced by sediment or other sample residue remaining in the hydraulic portions of the instrument for too long a period of time.

After the flush cycle 368 has been completed, the processor checks the TIME register to determine if the machine has warmed up for the required amount of time, denoted as $T_w$, block 396. If the required warm-up time has not passed, the processor will enter loop 398 and alternately display "WARMING UP", block 400, and check whether the required warm-up time has passed, block 402.

When the machine has warmed up for the required amount of time, the processor will display "RUN SELF-TEST", block 404, and enter loop 406. Loop 406 permits the operator to choose one of three modes for the instrument to enter. If the operator wants to wait before having the instrument proceed further, the STANDBY button is pressed, block 408, and the instrument enters standby mode, block 410, described below. If the operator wishes to turn off the machine, the CLEAN button is pressed, block 410; and the instrument jumps to clean mode, block 412, described below. Normally, the operator will press the SELF-TEST button, block 414, and the machine will proceed into self-test mode, block 416.

To run a self-test, the operator places a beaker of diluant with lysing agent under the snorkel and presses the SELF-TEST button. The instrument then proceeds to carry out the steps shown in FIGS. 7A and 7B. The first step in the self-test sequence is to carry out a prime cycle, block 420. The prime cycle is carried out by the instrument in several different modes and is performed by a sub-routine within processor 100.

Figure 8:
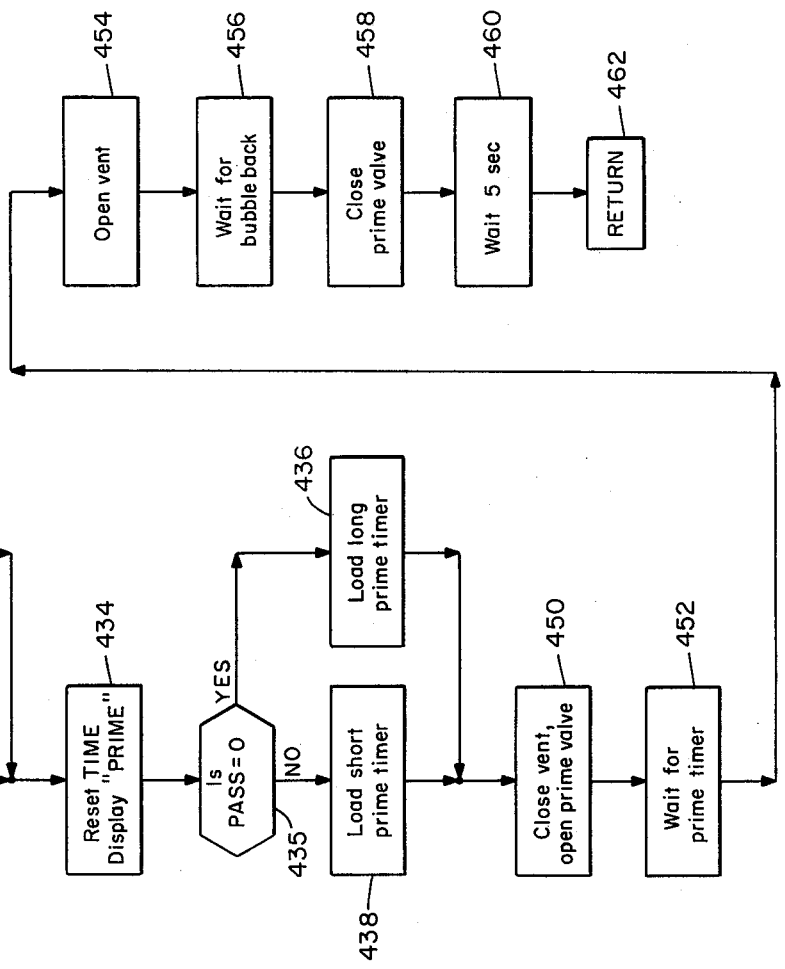
FIG. 8 is a flow diagram showing the steps carried out by the invention during a prime cycle.

FIG. 8 is a flow diagram of the steps performed by processor 100 during a prime cycle, which will now be described. In FIG. 8, the prime cycle begins be determining whether the last mode of the instrument was standby mode, block 430. If the last mode was standby mode, the instrument proceeds to clear transducer 34 and volumetric tube 54 of deionized water by turning on vacuum pump 32 and opening vent 51 for five seconds, block 432. If the last mode was other than standby, the instrument resets the TIME register and displays "PRIMING" in display 149, block 434.

The instrument next checks the PASS register, block 434. As will be described in greater detail below, if a malfunction is detected during a sample run, the instrument will so indicate and attempt to run the sample again. The PASS register indicates whether this is the first or a subsequent run of a particular sample. If this is the first run of the sample, the processor will load a longer time into the register which is later compared with the TIME register in timing the priming flow. This results in a longer prime flow to insure that remnants of the previous sample are completely flushed from the system, block 436. If the run is not the first run of a sample, the register used to time the prime flow is loaded with a shorter time, block 438.

After the prime timing register is loaded, vent 51 is closed and prime valve 48 is opened, block 450. The sample liquid is then primed through sample probe 30, transducer 34, the HGB cell 38 for a period determined by the time previously loaded into the prime timing register. After the prime flow has occurred for the proper time, block 452, vent 51 is opened, block 454. During the time that vent 51 is open, air rushes through vent 51 clearing orifice 52, block 454. After a one second delay, block 456, prime valve 48 is closed, block 458. The instrument waits for five seconds during which time air is drawn in through vent 51 clearing transducer 34 and volumetric tube 54, block 460; and the processor returns to the cycle from which it jumped to the prime sub-routine, block 462.

Referring again to FIG. 7A, after carrying out a prime cycle, block 420, the instrument displays "SELF-TEST IN PROGRESS", block 470. At this time volumetric tube 54 contains no liquid since it has been cleared during the prime cycle. With no liquid in the volumetric tube 54, light from each of the light sources 58B, 60B, and 62B is not transmitted to the respective photocells 58A, 60A and 62A. The output of each of these photocells is checked, blocks 472, 474 and 476. An indication from any of the photocells is indicative of a malfunction; and the instrument will proceed to a pass-check sub-routine, described in detail below, to alert the operator of the malfunction, blocks 478, 480 and 482. Otherwise, the processor will turn on current source 56 and close vent 51 to begin the sample flow through transducer 34 and volumetric tube 54, block 484.

The instrument next carries out the first flow check routine, block 486. The output from photocell 58A is monitored in loop 489 by the processor to determine when photocell 58A is turned on, block 488. This will occur when the sample flow in volumetric tube 54 reaches photocell/light source pair 58 and conducts light source 58B to photocell 58A. If the first photocell does not turn on within a predetermined time $T_1$, block 490, the instrument determines that a malfunction has occurred. The processor then proceeds to loop 491 and checks to see if the second photocell 60A has turned on, block 492, in which case the processor goes to the pass-check routine and indicates to the operator that the first photocell/light source pair is burned out, block 494. If the second photocell 60A does not turn on within a predetermined time, $T_2$, block 496, the processor goes to the pass-check routine and indicates to the operator that there is a slow flow, block 498.

If the first photocell 58A is turned on by the sample flow within the proper time, the processor checks to ascertain that the photocell has not turned on too soon, block 500. If the flow reached photocell 58A before a predetermined minimum interval, $T_3$, the processor proceeds to the pass-check routine and indicates to the operator that the flow was too fast, block 502.

The actual time required for the sample flow to reach photodetector 58A will vary with minor variations in the vacuum produced by vacuum pump 32 and regulator 73. The time limits $T_1$ and $T_3$ within which the flow time must fall are approximately plus and minus 25% of the nominal expected flow time. Since the variables which affect flow time generally change slowly, once the flow time has been determined on a particular day, the variations in flow time for samples run on that day can be expected to fall within tighter limits. Accordingly, once the nominal flow time to the first photodetector 58A has been determined by the flowcheck 1 routine, block 486, new maximum and minimum flow times $T_{MIN}$ and $T_{MAX}$ are calculated by the processor, block 504. These new maximum and minimum flow times are approximately plus and minus 10% of the flow time measured during the self-test mode. These stricter flow time limits are used during subsequent sample runs to ascertain that the sample flow is proceeding properly. At the end of the flow-check 1 routine, the TIME register is reset, block 506.

The instrument next resets counter 160 and A/D converter 118, block 508. Multiplexer 116 is set to apply the offset test voltage to A/D converter 118, and pulse generator 128 is commanded to send out a test pulse, block 510. Referring back to FIG. 3, the test pulse from pulse generator 128 is applied to amplifier 104 and thence to comparator 106 where it causes the output of comparator 106 to trigger control circuit 114. This control circuit initiates the analog to digital conversion in A/D converter 118.

The processor then waits for an end of conversion (EOC) signal for A/D converter 118. This done by an EOC-check sub-routine, block 512. In this sub-routine, the processor enters loop 514 where it repeatedly checks to see if the EOC signal has been generated by A/D converter 118, block 516, and then checks to determine that the time required by A/D converter to complete the conversion has not exceeded a preset maximum time, $T_4$, block 518. If the time to perform the conversion exceeds $T_4$, the processor will go to the pass-check routine and indicate to the operator that no EOC signal has occurred, block 520.

If the EOC signal is received within the proper time, the processor sets A/D multiplexer 116, to apply the gain-calibration input to A/D converter 118, block 522. The processor next reads the output of A/D converter resulting from the previous test pulse, calculates the A/D converter offset from that reading and stores the offset, block 524. Performing these operations in block 524 after switching multiplexer 116 to the gain position allows transients resulting from the switching of multiplexer 116 to settle while other operations are being performed and before a signal of interest is transmitted to A/D converter 118.

The processor next sends a signal to pulse generator 128 causing it ot produce a test pulse. This pulse causes control circuit 114 to start a conversion in A/D converter 118, and the processor enters an EOC-check sub-routine as described above, block 526. After the EOC signal has been received, the processor reads the output from A/D converter 118 therefrom, and stores this value of the gain, block 530.

The processor then checks the A/D offset, block 536. If it is determined that this offset is too large, the processor proceeds to the pass-check sub-routine, block 538 and indicates to the operator that the A/D converter offset is too large. If the offset is within specification, the processor next calculates the actual gain of the A/D converter by subtracting the offset from the gain read previously, block 540. The actual gain is checked to see that it is within predetermined limits, block 542. If the gain is out of spec, the processor proceeds to the pass-check routine and indicates this to the operator, block 544. Otherwise, the processor proceeds as described below.

The operations performed by the processor between the time that the flow reached the first photocell and this point in the flow diagram require only a few milliseconds to carry out. The processor next proceeds to a second flow check sub-routine flow-check 2, block 548, which is similar to the flow check sub-routine shown in box 486. The flow-check 2 sub-routine checks to determine that the flow time between the first photocell 58A and the second photocell 60A is within predetermined limits and similarly to flow-check 2, sets tighter limits for the minimum and maximum flow times based on the actual flow time as measured in the flowcheck routine, which tighter limits are used in subsequent sample runs. The flow time from photocell 58A to photocell 60A is approximately $3\frac{1}{4}$ seconds. During the time that the sample liquid is flowing between the first photocell 58A and the second photcell 60A, the particle counting apparatus of the instrument consisting of transducer 34, current source 56, and the associated electronics as shown in FIG. 3 have been enabled, and some counts will be registered by the instrument even through the liquid introduced for the self-test cycle contains no cells. When the flow reaches the second photocell 60A, the processor reads counter 120 and stores this value as the WBC background count, block 550. The processor next resets counter 120 and causes threshold control 108 to set the RBC threshold, block 552. The instrument will now proceed to take a RBC background count as the sample flows from the second photocell 60A to the third photocell 62A.

The processor subtracts two from the WBC background count stored previously, block 554. This is to compensate for the two test pulses from pulse generator 128 used by the processor in determining the A/D offset and gain. The processor next checks to determine that the WBC background count does not exceed a predetermined limit, block 556. If this limit is exceeded, the processor proceeds to the pass-check routine and indicates to the operator that the WBC background count is too high, block 558. Otherwise, the processor appropriately scales for display the WBC background count stored in memory, and the instrument displays the WBC background count to the operator along with a message indicating that the displayed value is the WBC background count, block 560. (The WBC background count may be as high as three or four percent of the WBC for low WBC's, and the operator may want to subtract this background count.) The processor next enters flow-check 3 sub-routine similar to the previous flow-check subroutines, block 562. The flow-check 3 sub-routine similarly determines that the flow time between the second photocell 60A and the third photocell 62A falls within acceptable limits. Flowcheck 3 differs slightly from the previous flow-check sub-routines in that if the flow from the second photocell to the third photocell exceeds a very long time limit, the instrument will indicate to the operator that the third photocell/light source pair is out; while if the flow time is too large but does not exceed this very large time limit, the instrument will indicate that a slow flow has occurred.

After the flow has reached the third photodetector 62A, the RBC background count is read from counter 120 and stored by the processor, block 564. The processor then checks to determine that the RBC background count does not exceed a predetermined limit, block 556. If the RBC background count is too large, the processor proceeds to the pass-check sub-routine and indicates this to the operator, block 568. Otherwise the processor appropriately scales the stored RBC background count, and the instrument displays the value to the operator along with an identifying legend on display 149, block 570.

The self-test cycle next proceeds to test the MCV circuitry of the instrument. Current source 56 is turned off, speaker 124 is turned on, and A/D multiplexer 116 is set to the MCV input so that the output of peak and hold circuit 112 is applied to the input of A/D converter 118, block 572. Counter 120 is reset, and the processor loads the appropriate values into test-pulse-counter registers used in producing the proper number of test pulses, block 574.

The processor next proceeds to loop 575 where the test pulses are generated. First, the processor causes pulse generator 128 to send out a test-1 pulse. This pulse is amplified by amplifiers 104 and 110, applied to peak and hold circuit 112 and the output of peak and hold circuit 112 is applied through A/D multiplexer to A/D converter 118. The output of amplifier 104 is also applied to comparator 106 which triggers control circuit 114 upon the occurrence of a pulse, which control circuit properly activates peak and hold circuit 112 and causes A/D converter 118 to begin a conversion at the proper time. The output of comparator 106 also clocks counter 120. After the test-1 pulse has been produced by pulse generator 128, the processor carrier out an EOC check, block 576. After an EOC signal has been received by the processor, the processor determines if 3,200 A/D outputs have yet been summed, and if not, the A/D output is added to the previously accumulated total, block 578. The processor next causes pulse generator 128 to send out a test-2 pulse, which pulse is smaller than the previous test-1 pulse. This pulse proceeds through the electronics of the instrument as described above, and the processor again performs an EOC-check, block 580. When the EOC signal is received from the A/D coverter 118, the processor again determines if 3,200 A/D outputs have been summed, and if not, the A/D output is added to the previously accumulated total, block 582. The processor next checks to see if loop 575 has been done 5,000 times, block 584. If not, the processor proceeds back to block 576 and repeats the above-described procedures.

After loop 575 has been repeated 5,000 times, the processor proceeds to the next step. By repeating loop 575 5,000 times, the processor has produced 10,000 test pulses of alternate large and small size for testing the electronics of the instrument. The magnitude of 3,200 of these pulses has been determined by A/D converter 118 and these magnitudes summed by the processor.

After finishing loop 575, speaker 124 and threshold control 108 are turned off, block 586. Vent 51 is opened to clear transducer 34 and volumetric tube 54 in preparation for the next sample flow, block 588. The number in counter 120 is checked to determine that it is within plus or minus 50 counts of 10,000, block 590. If the number in counter 120 is outside this range, the instrument proceeds to the pass-check routine and indicates to the operator that there was a test count error, block 592. If counter 120 contains the proper value, the instrument checks to see that the MCV accumulated by the processor is within the proper limits, block 594. If the MCV value falls outside these limits, the processor goes to the pass-check routine and indicates an MCV test error to the operator, block 596.

Otherwise, the processor proceeds to set multiplexer 116 to HGB and to clean A/D 118, block 598. The processor next sends out a test pulse to begin the A/D conversion, and performs an EOCcheck, block 600. After the EOC signal is received, the output of A/D converter 118 is read and the logarithm of the HGB value stored, block 602. This value is the zero HGB reading. The zero HGB reading is checked to determine that it falls within predetermined limits, block 604. If it does not, the instrument proceeds to the passcheck routine, block 606. If the zero HGB reading is within the proper limits, the instrument proceeds to wait mode, block 610.

Figure 9:
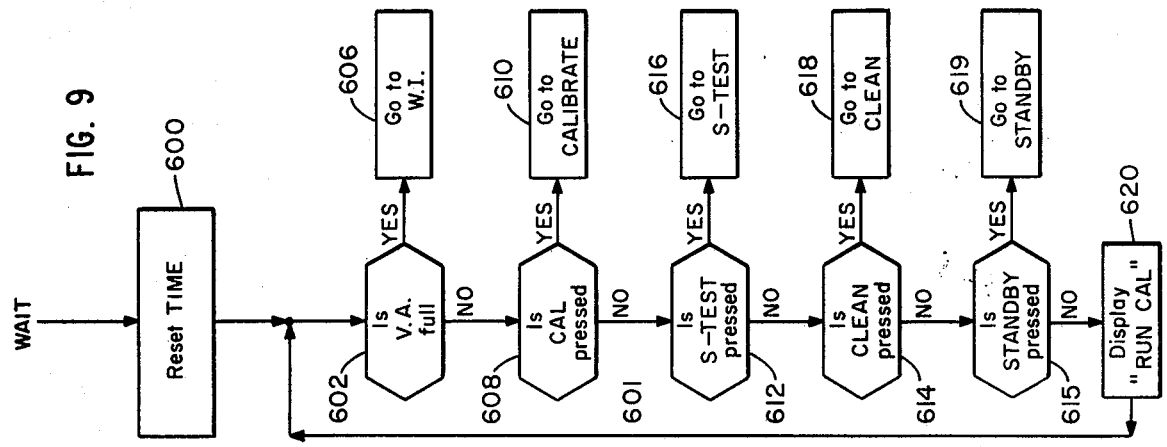
FIG. 9 is a flow diagram showing the steps carried out by the invention during wait mode.

FIG. 9 shows the steps carried out by the processor while the instrument is in the WAIT state. The WAIT state is initiated by resetting the TIME register, block 600. Next, the instrument proceeds to check vacuum accumulator 46, block 602. If the vacuum accumulator is full, the processor jumps to the waste interrupt subroutine, described in greater detail below. If vacuum accumulator 46 is not full, the processor continues in loop 601 until the operator presses a button corresponding to an allowed cycle. In this manner, the instrument insures that the proper procedures are carried out before sample testing is done. In loop 601, the instrument checks to see if the front panel calibrate button has been pressed, block 608. If the calibrate button has been pressed, the instrument will proceed to perform a calibrate cycle, block 610. Otherwise, the instrument will check to see if the SELF-TEST button has been pressed, block 612, or the CLEAN button has been pressed, block 614, or the STANDBY button has been pressed, block 615; and if any of these buttons has been pressed, the instrument will proceed to the appropriate cycle, blocks 616, 618, and 619. If the operator has not pressed a button corresponding with an allowed procedure which the instrument may carry out at this point, the instrument displays "RUN CAL TESTS", block 620, and repeats loop 601.

Figure 10:
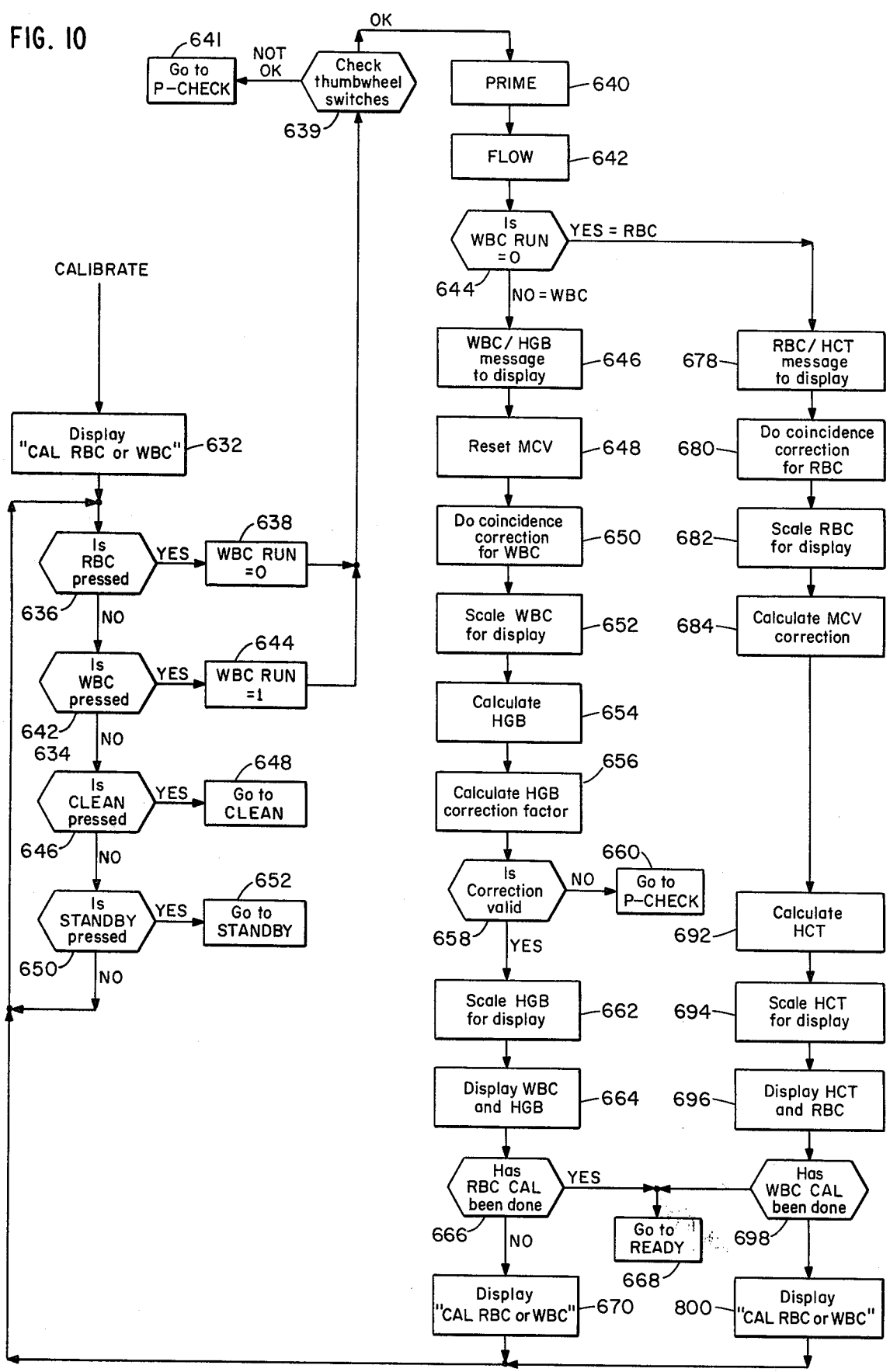
FIG. 10 is a flow diagram showing the steps carried out by the invention during a calibration cycle.

Normally, an operator will proceed from the wait state shown in FIG. 9 to the calibrate cycle. Referring to FIG. 10, the steps carried out by the processor during a calibrate cycle are shown in greater detail. The machine first displays to the operator "CALIBRATE RBC OR WBC", block 632. The processor proceeds to loop 634 and proceeds to test each of the front panel buttons corresponding with an instrument cycle to which the machine is allowed to proceed. If the front panel RBC button is pressed, block 636, the processor sets WBCRUN register to 0, block 638, and proceeds to block 639. Otherwise, the processor checks to see if the WBC button has been pressed, block 642. If the operator has pressed the WBC button, the WBCRUN register is set to 1, block 642, and the instrument proceeds to block 640.

If the operator wishes to shut down the instrument at this time, the operator may press the CLEAN button, block 646, and the machine will proceed to the CLEAN cycle, block 648. The operator may also proceed to standby mode by pressing the STANDBY button, block 650, and the machine will proceed to standby mode, block 652. The processor will continue to repeat loop 634 until a permitted button is pressed by the operator.

Normally, the operator will elect to perform either a WBC calibration or a RBC calibration, and the machine will proceed to check the front panel HGB and MCV thumbwheel switches 89 and 90 to ascertain that they are within reasonable limits, block 639. If an error in either of these calibration values is detected, the instrument proceeds to the pass-check routine where it so notifies the operator and then halts, block 641. Otherwise, the instrument proceeds to perform a prime cycle, block 640, as described above. After performing the prime cycle, the instrument will perform a flow cycle, block 642, described in greater detail below. It is during the flow cycle that the various different measurements which the machine performs are accomplished. After performing the flow cycle in block 642, the processor checks the WBCRUN register to determine whether a WBC calibration run or a RBC calibration run was previously indicated by the operator, block 644.

After the instrument has performed a WBC calibration run, the following steps are performed. First, the instrument loads display control 148 with the appropriate message for indicating the WBC and HGB values to the operator that were measured during the run, block 646. Next, the MCV register is reser to 0, block 648. The WBC is coincidence corrected, block 650. While this coincidence correction may be done in many ways, one particular method by which this coincidence correction may be carried out is described in greater detail below. Next, the coincidencecorrected WBC is scaled and formatted for display, block 652.

The HGB value is then determined by subtracting from the log of the zero HGB value, determined previously during the self-test cycle, the HGB value read during the flow cycle, block 654. The instrument calculates a correction factor by comparing the previously calculated HGB value with the actual HGB value of the calibration sample as indicated to the instrument on front panel thumbwheel switches 89, block 656. The processor checks to ascertain that this correction factor falls within predetermined limits, block 658, and if the correction factor is determined to fall outside of these limits, the processor proceeds to the passcheck routine where it indicates the occurrence of an HGB calibration error to the operator, block 650. Otherwise, the HGB value is properly scaled and formatted for display, block 622, and the WBC and HGB values previously measured and calculated by the instrument are displayed with the identifying messages previously sent to display 149 in block 646, block 664.

The machine then checks to see if an RBC calibration has been done, block 666. If both calibrations have been performed, the instrument proceeds to ready mode, block 668. Otherwise, the instrument displays "CAL RBC OR WBC", block 670, and returns to loop 634 until the operator presses an allowed button.

During an RBC calibration run, the processor carries out the following steps. First, the processor sends to display 149 the message which will be displayed to the operator along with the RBC and HCT values measured by the instrument, block 678. Next, the processor performs a coincidence correction on the RBC value measured during the flow cycle, block 680. The method by which this coincidence correction is performed is described in greater detail below. The coincidence-corrected RBC value is then scaled and formatted for display by the instrument, block 682.

The instrument next compares the measured value of MCV with known MCV value of the calibration sample as entered into the instrument by front panel thumbwheel switches 90 and from these two values calculates the MCV correction factor, block 684. From the MCV correction factor, the instrument calculates the HCT value, block 692, and this value is scaled and formatted for display, block 694. The processor then displays the measured and corrected values for RBC and HCT along with the identifying message previously stored, block 696. After displaying this information, the processor checks to determine if the WBC calibration has been performed, block 698. If both calibrations have been done, the instrument proceeds to the ready state, block 668; otherwise, the instrument displays "CAL RBC OR WBC" and returns to loop 634, block 800.

Figure 11C:
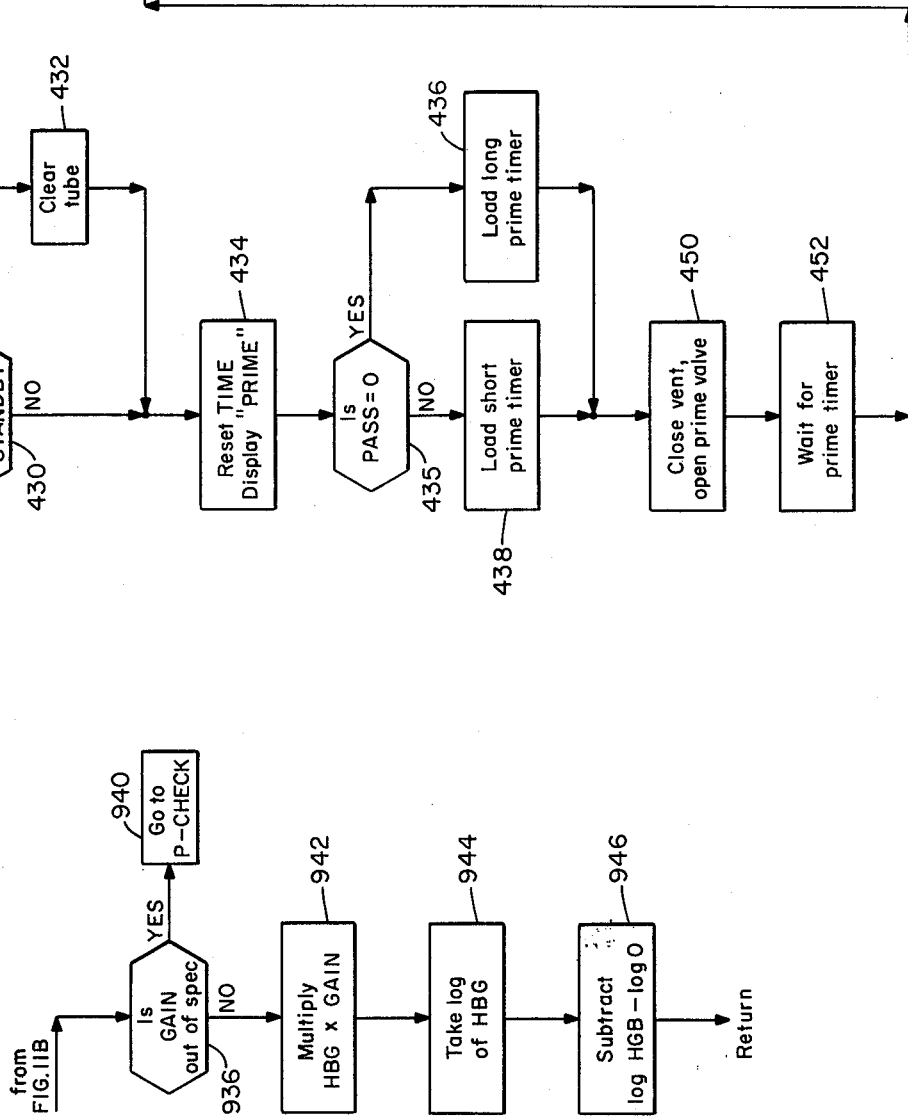
Figure 11A:
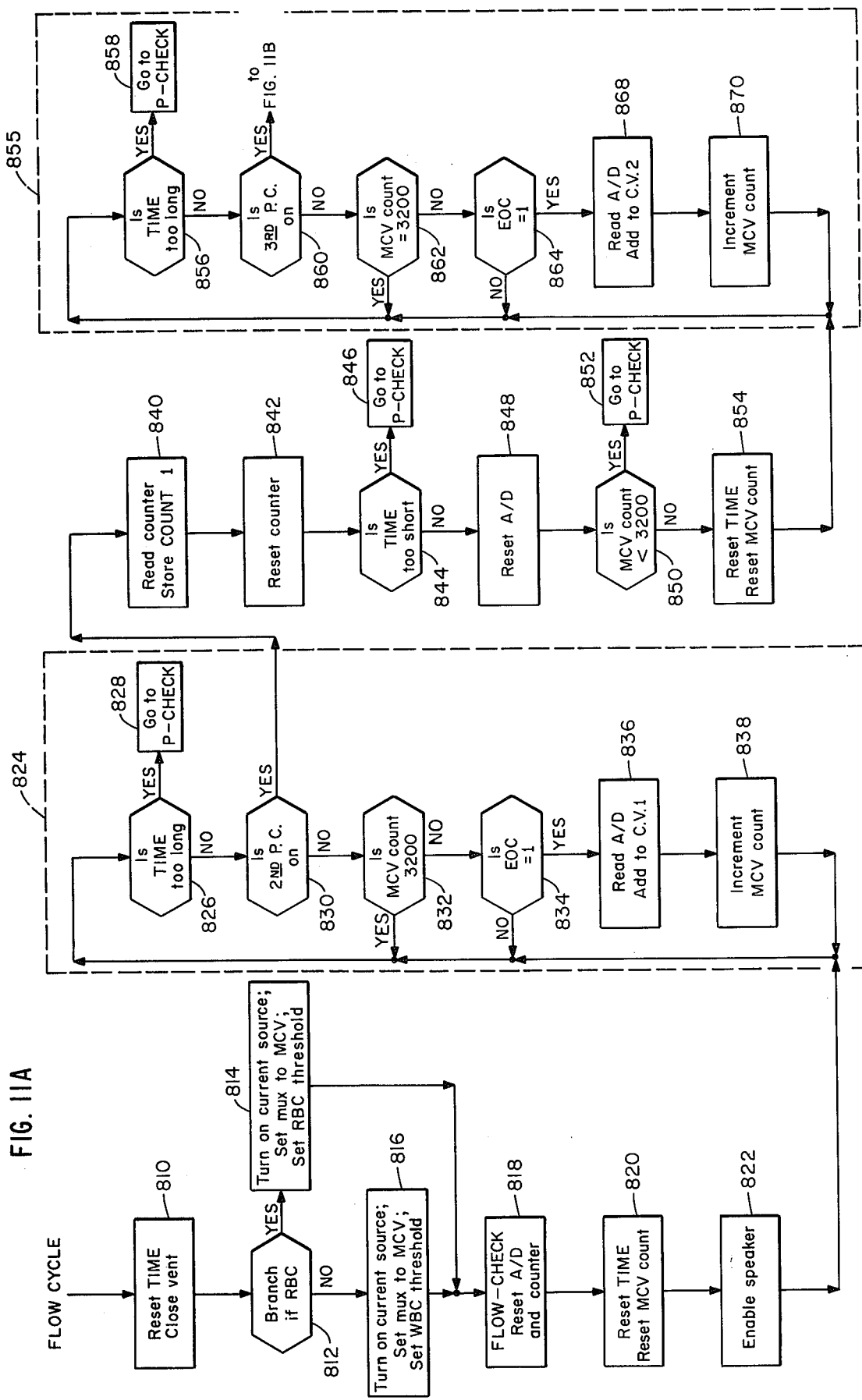

FIGS. 11A, 11B and 11C show the steps carried out by the instrument in performing a flow cycle. First, the TIME register is reset and the sample flow is begun by closing vent 51, block 810. The processor checks to see if an RBC or WBC analysis is being run, block 812. If the processor is performing an RBC, the instrument turns on current source 56, sets A/D multiplexer 116 to MCV, and sets threshold control 108 to the RBC threshold, block 814. If the instrument is performing a WBC run, the instrument turns on current source 56, sets the A/D multiplexer to MCV and sets threshold control 108 to the WBC threshold level, block 816. Blocks 814 and 816 are configured as shown due to the fact that one data word is used to perform all the functions shown within these blocks, different bits in this data work being operative to turn on and off current source 56, set multiplexer 116 and determine the threshold value of threshold control 108.

The processor next performs a flow check routine similar to flow-check 1 shown in FIG. 7 and described above, to ascertain that the flow reaches the first photodetector 58A within the specified time limits, block 818. If the flow time is out of spec, the processor goes to the pass-check routine and the instrument so notifies the operator on display 149. Otherwise, A/D converter 118 and counter 120 are reset, block 818. The TIME register is reset, and if an RBC is being done, the MCV-count registers are reset, block 820, speaker 124 is enabled, block 822.

The instrument then proceeds to block 824 wherein the sample measurements are taken as the sample flow proceeds from the first photocell 58A to the second photocell 60A. First, the processor checks that the flow time from the first photocell to the second photocell has not exceeded the limit determined during the previously performed self-test cycle, block 826. If this time limit is exceeded, the instrument proceeds to the pass check routine, block 828. Otherwise, the instrument checks to determine if the flow has yet reached the second photocell 60A, block 830. If the second photocell has been reached, the processor leaves block 824 and proceeds as described below.

If the flow has not yet reached the second photocell, the processor next checks to see if the MCV count has reached 3,200, block 832. During RBC runs, each time a pulse is registered by transducer 34 and the pulse height converted by A/D converter 118, the digital value representing the pulse height is read by the processor. The processor totals 3,200 of these pulse heights to produce the MCV value. Simultaneously, the processor is counting the number of particles detected by transducer 34 for a particular volume of the sample fluid, as measured by volumetric tube 54. Since the pulses from transducer 34 occur at somewhat irregular intervals, and since the analog-to-digital conversion performed by converter 118 takes a finite amount of time, the 3,200 pulses summed by the processor to produce an MCV value are not necessarily the first 3,200 pulses counted by the instrument to produce a WBC or RBC. The MCV-count register contains the number of pulse heights from A/D converter 118 which ahve been summed by the processor. When 3,200 pulse heights have been summed, the processor branches back to block 826 from block 832 and proceeds to perform the loop defined by blocks 826 through 832 until the flow reaches the second photocell. During this time, counter 120 continues to count the particles detected by transducer 34. For WBC runs, the MCV-count register is initially set to 3,200 in block 820, and blocks 834 – 838 are not performed.

If the MCV register has not reached 3,200, the processor checks to determine if the EOC output from A/D converter 118 is a logical 1, signifying that an analog value has been converted and is ready to be entered into the processor, block 834. If no value is ready to be read, the processor returns to block 826. If a conversion is finished, the processor reads the A/D output and adds this value to the total cell volume accumulated in register C.V.1, block 836. The MCV count is incremented by 1, block 838, and the processor returns to block 826.

When the instrument detects that the sample flow has reached the second photocell 60A, block 830, the processor reads counter 120 and stores this value in the COUNT 1 register, block 840; and the counter is reset, block 842. If the time of the sample flow between the first photocell 58A and the second photocell 60A was too short, block 844, the processor proceeds to the pass-check routine, block 846. Otherwise, the processor resets A/D converter 118, block 850.

Next, the MCV count register is checked by the processor, block 850. If less than 3,200 pulses were read from A/D converter 118, the processor proceeds to the pass-check routine, and alerts the operator to an MCV count error, block 852. Otherwise, the processor resets the TIME register and resets the MCV count register if an RBC run is being done, block 854.

The processor next proceeds to carry out the operations contained within block 855. Block 855 corresponds to the flow of the sample between the second photodetector 60A and the third photodetector 62A and is practically identical with block 824 described in detail above. Accordingly, the processor checks the TIME register, block 856, and if the flow time was too long, proceeds to the pass-check routine, block 858. Otherwise, the processor checks the third photocell 62A, block 860. When the flow reaches the third photocell, the processor leaves block 855. If the sample flow has not reached the third photocell, the processor checks to determine whether the MCV count register has reached 3,200, block 862. If the cell volume of 3,200 cells have been summed, the processor returns to block 856. Otherwise, the processor proceeds to block 864 and checks A/D converter 118 to determine if it has finished a conversion. If no conversion has been finished, the processor returns to block 856. Otherwise, the output of A/D converter 118 is read and added to the previously accumulated total cell volume stored in register C.V.2, block 868. The MCV count register is incremented, block 870, and the processor returns to block 856.

When the sample flow reaches the third photocell 62A, the processor reads the value in counter 120 and stores this value in register COUNT 2, block 872. The processor then disables speaker 124 and sets multiplexer 116 to the HGB state, block 874. The TIME register is checked to ascertain that the flow time between the second and third photodetectors was not too short,
block 876. A short flow time causes the processor to proceed to the pass-check sub-routine, block 878, and the instrument alerts the operator to a fast flow. Otherwise, A/D converter 118 is read to reset it, block 880. The processor commands pulse generator 128 to produce a test pulse, block 882, triggering A/D converter 118. The processor performs an EOC check routine, described above, and reads the HGB output from A/D converter 118 which is stored in the HGB register, block 884. Next, vent 51 is opened allowing air into transducer 34 and clearing volumetric tube 54, block 886.

The processor next compares the cell count measured during the first flow between the first and second photocells with the cell count measured during the second flow between the second and third photocells. First, the cell volume total from the first flow stored in register C.V.1 and the cell volume total from the second flow stored in register C.V.2 are averaged, block 888. Next, the processor subtracts the cell count measured during the second flow, COUNT 2, from the cell count measured during the first flow, COUNT 1, to find the difference between these counts; and the absolute value of this difference is computed, block 890. The processor calculates 12% of the count measured during the first flow, block 892. If the difference between the counts measured during the first and second flows exceeds 12% of the count measured during the first flow, block 894, the instrument goes to the pass-check routine and informs the operator that the two measurements do not agree, block 896. Otherwise, the instrument computes the average of the counts measured during the first and second sample flow, block 900.

Next, the instrument checks to determine whether a WBC or an RBC run is being performed by the instrument, block 902. For a WBC run, if the average count calculated in block 900 is greater than 5,000 cells, block 904, the processor calculates 6% of the count measured during the first flow, block 908, and checks to ascertain that the difference between the counts measured during the first and second flow is less than 6% of the count measured during the first flow, block 910. If the difference is greater than 6%, the instrument proceeds to the pass-check routine, and notifies the operator that the two measurements do not agree, block 912. For an RBC run, if the measured average count is more than 2,000 cells, block 906, the processor checks to determine that the counts measured during the first and second flow do not differ by more than 6%, as described above, blocks 908 – 912.

Otherwise the processor proceeds to block 914 where multiplexer 116 is set to apply the offset test voltage to A/D converter 118; and A/D converter 118 is cleared. The processor causes pulse generator 128 to send out a test pulse, starting a conversion in A/D converter 118, block 916. After converter 118 has produced the EOC signal, the converted value is read by the processor, block 918, and this value is stored, block 920. The processor checks to determine whether the offset voltage of A/D converter 118 is too large, block 922. If the offset voltage is out of spec, the processor proceeds to the pass-check routine and displays to the operator that the offset voltage is too large, block 924. Otherwise, the processor sets multiplexer 116 to the GAIN position, block 926.

A/D converter 118 is cleared and pulse generator 128 sends out another test pulse, block 928. The processor waits for the EOC signal from A/D converter 118 and reads the converted value therefrom upon the occurrance of the EOC signal, block 930. This value is stored, block 932, and the processor calculates the corrected gain by subtracting the offset voltage from the measured gain, block 934. If the calculated value of the A/D gain is out of spec, block 936, the processor goes to the pass-check routine and displays to the operator that the A/D gain is out of spec, block 940.

Otherwise, the measured HGB value previously stored, block 884, is multiplied by the corrected value of the gain, block 942. The logarithm of the HGB value is taken by the processor, block 944, and the logarithm of the measured HGB value is subtracted from the logarithm of the previously measured zero HGB value to produce the final value of HGB, block 946. This concludes the flow routine and the processor returns to the point from which it entered the flow routine.

FIG. 12 shows one method by which the coincidence correction of the measured RBC and WBC values may be performed. The instrument first checks to determine that the measured count is not too high, block 952. If the measured count exceeds the prescribed limit, the processor goes to the pass-check routine and informs the operator of a dilution error, block 954. If the count falls within the prescribed limit, the processor proceeds to block 956 where the measured count is squared and this value is stored.

Next, the measured count is cubed and stored, block 958. The processor calculates the value of $a_1 x$, block 960, where $a_1$ is a coefficient as described below. This intermediate value is stored in Y register, block 962. The processor next calculates the value of $a_2 x^2$, block 964, and adds this value to the previously stored value in the Y register, block 966. Next, the value of $2_3 x^3$ is calculated, block 968, and this value is added to the value in the Y register, block 970. Finally, the value in the Y register is properly scaled to produce the coincidence corrected count, block 972. The coefficients $a_1$, $a_2$, and $a_3$, will vary depending on the characteristics of the transducer 34, the dilution ratio and upon the particular analysis being done RBC or WBC.

While other methods of performing coincidence corrections may be employed with the invention, such as look-up tables stored in ready-only memory, as shown in U.S. Pat. No. 3,864,551, the method shown in FIG. 12 has the advantage of requiring less memory than would a look-up table-type or correction scheme.

Figure 13:
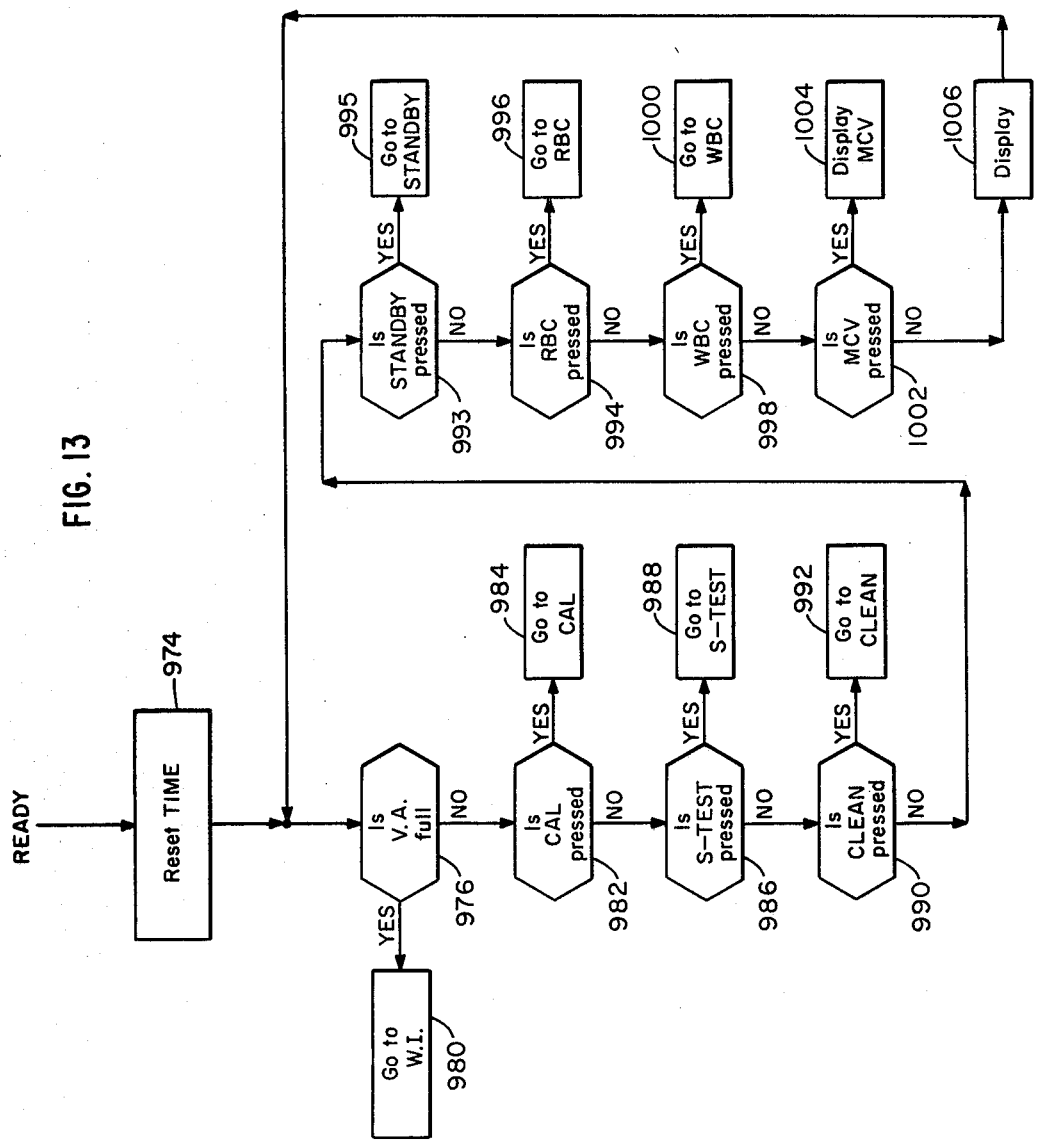
FIG. 13 is a flow diagram showing the steps carried out by the invention during ready mode.

After the processor has completed the calibration cycle and between RBC and WBC sample runs, the instrument is normally in ready mode. FIG. 13 shows the procedure carried out by the processor when the instrument is in ready mode. First the TIME register is reset, block 974. Next, the instrument checks to determine whether the vacuum accumulator is full, block 976. If the vacuum accumulator is full, the processor branches to the waste interrupt routine, described in detail below, block 980.

Otherwise, the processor proceeds to sequentially check each of the front panel buttons until an operator presses one of the buttons designating the procedure which the instrument is to next perform. Accordingly, the processor checks to determine if the front panel CALIBRATE button is pressed, block 982, and if so, proceeds to the calibrate cycle, block 984. The processor next checks the SELF-TEST button, block 986, and if the operator has pressed this button, the processor goes to the self-test cycle, block 988. If the operator has pressed the CLEAN button, block 990, the instrument proceeds to a clean cycle as described below, block 992. The STANDBY button is checked, block 993; and if it is pressed, the instrument goes to standby mode, block 995.

Normally, after the instrument has been calibrated, the operator will proceed to perform a WBC or RBC sample run. To perform an RBC, the operator presses the front panel RBC button, block 994, and the instrument proceeds to perform an RBC sample run as described below, block 996. If the operator presses the front panel WBC button, block 998, the instrument will perform a WBC sample run, described below, block 1000.

When an RBC sample run is performed, the instrument will automatically display the measured values of RBC and HCT. To display the MCV value, the operator presses the front panel MCV button 94 after the machine has performed the RBC sample run and has returned to ready mode, block 1002. The processor will display the measured value of MCV as long as the button is depressed, block 1004. If the instrument previously performed a WBC run, the instrument will display "NO MCV".

If no buttons have been depressed, the processor goes to the display routine, described in greater detail below, where the values measured during the previous sample run, RBC/HCT or WBC/HGB, are displayed, block 1006. The precessor then returns to block 976 and repeats the above-described sequence of operations.

FIG. 14 shows the steps carried out by the instrument in performing a WBC sample run. The operator initiates a WBC sample run by immersing sample probe 30 in a properly diluted sample and pressing the front panel WBC button 95. The instrument then performs a prime cycle, block 1010. After the prime cycle is completed the instrument performs a flow cycle during which time WBC and HGB measurements of the sample are taken, block 1012.

The processor next checks to ascertain that the calibration run has been properly performed, block 1014. As described in greater detail below, an operator may have the machine perform a WBC even though the calibration cycle has not been successfully carried out. Since the proper operation of the cell-counting sections of the instrument is verified during the self-test cycle, the instrument is able to perform a cell count even though calibration of the HGB measurement apparatus has not been done. If a proper calibration of the HGB measurement apparatus has not been performed, this is determined in block 1014, and the instrument will set a flag which prevents the measured HGB value from being displayed to the operator. Otherwise, the instrument will display both the WBC and HGB values upon the completion of a WBC sample run, as described below.

Next, the instrument loads the display message tables 148 with the appropriate messages for indicating the WBC and HGB values to the operator, block 1016. The measured value of WBC is coincidence corrected, block 1020; and the instrument properly scales and formats the corrected WBC count for display to the operator, block 1022. Next, the HGB value is calculated from the measurement made during the sample run, block 1024. The HGB value is properly scaled and formatted for display to the operator, block 1026.

The instrument then returns to ready mode. The measured values of HGB and WBC are actually displayed to the operator during ready mode by the display routine therein.

FIG. 15 shows the steps carried out by the instrument in performing an RBC sample run. The steps are very similar to the steps previously described for the WBC cycle. To initiate an RBC sample run, the operator immerses sample probe 30 in a properly diluted sample and presses the front panel RBC button 93. The instrument performs a prime cycle, block 1028 followed by a flow cycle, block 1030. The instrument checks to ascertain that the calibration for MCV and HCT measurements has been properly carried out. If the calibration has not been properly performed, the processor sets a flag which prevents the instrument from displaying these parameters from the operator, and only the RBC count value is displayed by the instrument.

Next, the instrument loads the display routine with the appropriate message for indicating the RBC and HCT values to the operator, block 1034. The measured RBC is coincidence-corrected, block 1036; and the corrected RBC value is properly scaled and formatted for display, block 1038. The instrument next calculates the MCV from the measurements made during the flow cycle, block 1040. The HCT value is calculated by multiplying the previously determined RBC and MCV values, block 1042. The HCT value is properly scaled and formatted for display, block 1044; and the processor returns to ready mode. The RBC, HCT, and MCV values are displayed by the instrument during ready mode.

FIG. 16 shows the display routine performed by the instrument in displaying the various values and messages to the operator. When anything is to be displayed to the operator, the processor will first load the appropriate message into the display message tables, as described below, and then jump to the display routine shown in FIG. 16 which performs the functions described below.

The processor first checks to determine that the display routine was last performed, block 1050. This is for the following reason. Front panel display 149 is typically of the type which will continue to display a message without requiring refresh after the electronic signals representative of that message are no longer applied to the display. In many of the procedures carried out by the processor, the processor will repeatedly cycle around a loop which includes a display step until one or more required events are detected, usually the depressing of a front panel control button by the operator. An example of this type of operation is found in FIG. 13 which shows the steps carried out by the processor when the instrument is in ready mode. As can be seen from FIG. 13, each time the processor completes a loop, it will branch to the display routine in block 1006. The time required by the processor for completing all the steps of this loop is on the order of hundreds of microseconds, and therefore the loop will branch to the display routine several thousand times times per second. Since the front panel display 149 does not require refresh, it is not necessary that the display routine be carried out this often. The time check performed in block 1050 solves this problem by only permitting the complete display routine to be performed if a predetermined interval has passed since the last time the display routine was performed. Accordingly, the time check in block 1050 will only branch to block 1052 and the remainder of the display routine if it is determined that the display routine has not been performed within a previous predetermined amount of time, typically approximately four seconds. Otherwise, the time check in block 1050 will cause the processor to immediately return to the point from which it branched to the display routine.

If the processor does not return in block 1050, the display routine next checks to determine whether one or two messages are to be displayed, block 1052. Certain cycles and operations of the instrument cause two messages to be alternately displayed to the operator. These cycles include: RBC sample runs, in which the instrument alternately displays to the operator the measured RBC value and the measured HCT value; WBC sample runs, in which the instrument alternately displays the measured WBC value and the measured HGB value; and verify routines in which the instrument first displays to the operator the detected malfunction and then displays a message instructing the operator as to corrective action to be taken. This is determined by checking the flash flag indicating that two messages are to be displayed when it is set.

If two messages are to be displayed, the processor proceeds to block 1054. From block 1054 the display routine alternates between block 1056, displaying the first message, and block 1058, displaying the second message on alternate passes. Since, as explained above, the complete display routine is carried out only approximately every four seconds, the result is that the two messages are alternately displayed to the operator by the instrument, each message having a duration of approximately four seconds. The first and second messages in block 1056 and 1058 are stored in the appropriate locations in memory called message tables, by the cycle which generates those messages, after which they are displayed by branching to the display routine which displays the message(s) stored at those location(s) in memory, as shown.

If the processor determines that only one message is to be displayed, block 1052, the instrument will only display the first message stored in memory, block 1056.

The processor next checks to see if the TIME register has exceeded forty-five seconds, block 1060. The TIME register is reset at the beginning of each cycle and thus serves to indicate how much time has passed since the last cycle has been performed by the machine. If the TIME register exceeds forty-five seconds, the processor proceeds to block 1062 where the TIME register is reset and a L-TIME register is incremented, for purposes described below. The processor next turns off vacuum pump 32, block 1064, and returns to the cycle from which it branched to the display routine.

If the TIME register does not exceed forty-five seconds, block 1060, the processor next checks to see if the L-TIME register exceeds ten minutes, block 1066. If not, the processor returns from the display routine. If the L-TIME register does exceed ten minutes, the processor loads the display with "CLEAN SYSTEM" and disables the flash flag, block 1068. The processor next turns on the buzzer, block 1070, and returns to the cycle which called the display routine. Subsequent passes through the display routine cause the "CLEAN SYSTEM" message to be displayed to the operator.

The result of blocks 1060 through 1070 is as follows. If no procedure is carried out by an operator for forty-five seconds, the instrument automatically turns off vacuum pump 32. If no procedure is carried out by an operator for ten minutes, the instrument alerts the operator by sounding a buzzer and indicates to the operator that the instrument should be cleaned. The operator may then proceed to put the instrument in standby mode or perform a clean cycle in preparation for shutting off the machine; or the operator may proceed to perform an RBC or WBC measurement cycle or any other cycle on the instrument.

Referring to FIG. 17, the operation of the instrument during a waste interrupt cycle is explained. Front panel waste switch 88 is connected to an interrupt input to the processor, and pressing switch 88 will cause the processor to immediately branch to the waste interrupt cycle. Additionally, vacuum accumulator 46 is checked by the instrument during several of the previously described cycles and modes, and if the instrument detects that vacuum accumulator 46 is full, the processor will branch to the waste interrupt cycle.

Upon branching to the waste interrupt cycle, the processor first disables the waste interrupt input connected to front panel waste switch 88. This is done to insure that the instrument will complete the waste interrupt cycle before the operator can again cause the instrument to begin a waste interrupt cycle. Next, the instrument clears the processor stack, block 1082, and stores the proper return address in the stack, block 1084. This prevents the instrument from returning to the middle of a routine at the completion of the waste interrupt cycle. The return address stored in the processor stack is determined according to the mode or cycle which the instrument was previously performing.

Next, the instrument determines if the waste interrupt routine was entered by aborting a WBC, RBC, self-test, or calibration run, block 1086. If a run was aborted, the processor clears the instrument by opening vent 51, allowing air into volumetric tube 54, block 1088. The processor then enables the waste interrupt input, block 1092, which was previously disabled in block 1080, and returns to the appropriate location, block 1094 as previously determined in block 1084. For example, if a WBC or RBC sample run were aborted, the processor would return to ready mode.

If the instrument determines that a run was not aborted, block 1086, the waste interrupt routine would normally have been entered by branching from a cycle which detected that the vacuum accumulator 46 was full. The processor then checks waste container 68 to determine if it also is full, block 1096. If waste container 68 is full, the instrument displays "EMPTY EXTERNAL WASTE", block 1098. The processor enables the waste interrupt input, block 1100, which was previously disabled in block 1080. The processor then stops, block 1102. In response to the display of the message "EMPTY EXTERNAL WASTE", the operator empties waste container 68. After the waste container has been emptied, the operator then presses front panel waste button 88. This causes the processor to branch to the beginning of the waste interrupt routine, and the waste interrupt routine is carried out to resume operation of the instrument.

If it is determined that the waste container is not full, block 1096, the instrument proceeds to empty vacuum accumulator 46. First, vacuum valve 72, pressure valve 74, and waste valve 64 are appropaiately set, as described above, to pressurize vacuum accumulator 46 and flush the sample waste therein into waste container 68, block 1104. While the vacuum accumulator is being emptied, the instrument displays "INTERNAL WASTE EMPTYING", block 1106. After thirty-five seconds, block 1108, vacuum valve 72, pressure valve 74, and waste valve 64 are reset, block 1110. The processor then proceeds to enable the waste interrupt input, block 1092, and returns to the appropriate cycle, block 1094.

To summarize the above described steps, pressing front panel waste switch 88 has one of three results, depending on when the switch is activated. If the waste switch is activated during a sample run, it causes the sample run to be aborted. If the external waste container 68 is full, the instrument alerts the operator to this fact and halts operation until the operator empties the waste container, and pressing the waste switch restarts the instrument. If a sample has not been aborted and the external waste container is not full, pressing the waste switch operates to empty the contents of vacuum accumulator 46 into waste container 68.

In response to the detection by the instrument of a malfunction or other error occurring during a self-test calibration, WBC or RBC cycle, the instrument goes to the pass-check routine, as has been explained above. The pass-check routine displays a message to the operator informing him of the malfunction which has occurred and then returns to the cycle being performed and attempts to repeat the cycle. If an error occurrs on the second attempt to perform a cycle, the instrument again proceeds to the pass-check routine. The pass-check routine displays a message to the operator indicating the malfunction which occurred and then displays a second message indicating the appropriate corrective action which the operator should carry out. After this, the instrument stops until the operator has carried out the required remedial action and restarted the machine by pressing an appropriate button.

This operation of the pass-check routine is shown in detail in the flow diagram of FIG. 18. The instrument begins the passcheck routine by storing an error code, generated by the malfunction detecting steps of the previous cycle, in an error register, block 1100. The processor then opens vent 51 to clear volumetric tube 54 and turns off current source 56 and speaker 124 block 1102.

The processor next checks a PASS register to determine the value thereof, 1104. The PASS register is used to keep track of the number of times a particular cycle has been attempted. During the first pass of the self-test cycle, the pass variable is zero. For the first attempt of all other cycles, the pass register equals one. This allows the self-test procedure to be repeated two times before the instrument will stop, in contract with all other cycles which are only repeated once.

If the processor determines in block 1104 that the pass variable equals zero, corresponding to the first attempt of a self-test cycle, the error code previously sotred in block 1100 is sotred in an ERROR-0 register, block 1106. Otherwise, the processor proceeds to block 1108 where it checks to determine if the PASS register equals one. If the pass register equals one, the error code stored in block 1100 is stored in an ERROR-1 register, block 1110.

From blocks 1106 and 1110, the processor proceeds to block 1112 where the errors stored in the ERROR-0 and ERROR-1 registers are compared. The only circumstances under which the ERROR-0 register will contain a value corresponding with a malfunction is if the self-test procedure is being performed. Thus, block 1112 determines whether in a second attempt of a self-test procedure the same error occurred as in the first attempt of the self-test procedure. In this case, the instrument will not make a third attempt to perform a self-test cycle, but instead will proceed to perform the steps in column 1114, explained below.

If the pass-check routine has been entered from the first attempt of a cycle other than a self-test cycle, the processor will go from block 1108 to block 1116, the steps in blocks 1110 and 1112 being meaningless except for self-test cycles. The processor will also proceed to block 1116 as described above after the first attempt of a self-test cycle or the second attempt of a self-test cycle where the same malfunction has not been repeated. In either event, the processor loads an error message indicating the particular malfunction which has occurred into the display message table, block 1116.

The processor then displays the error message to the operator, block 1118. The PASS register is incremented by one, block 1120, and the instrument attempts to repeat the cycle being performed previously. Accordingly, the processor checks to determine if the instrument was performing a self-test cycle, block 1112, and if so, returns to the self-test cycle, block 1124. The processor next checks to determine if the instrument was performing a calibrate cycle, block 1126, and if so, returns to the calibrate cycle block 1128. The processor next checks to determine if the instrument was performing a WBC sample run, block 1130, and if so, attempts to perform a successful WBC sample run, block 1132. Finally, the processor checks to determine if the instrument was performing an RBC sample run, block 1134, and if so, returns to reattempt an RBC sample run, block 1136.

If the processor determines that the PASS register exceeds one, block 1108, or if the same malfunction occurred during the first and second attempts at a self-test cycle, the instrument proceeds to perform the procedures shown in column 1114. First, the instrument loads an error message in display message table 1 for indicating to the operator the malfunction that occurred, block 1140. The instrument then loads into message table 2 a message indicating the appropriate corrective action which the operator should take, block 1142. The flash flag is set to cause both messages to be displayed, block 1144.

The instrument then jumps to the appropriate verify routine depending upon the cycle previously being attempted by the instrument. Accordingly, the processor checks to determine if the instrument was performing a self-test cycle, 1146, in which case the processor goes to the verify-1 routine described below, block 1148. The processor next checks to determine if the instrument was previously performing a calibrate cycle, block 1150, in which case the processor goes to the verify-2 routine described below, block 1152. The processor next checks to determine if the instrument was performing a WBC sample run, block 1154, or an RBC sample run, block 1158, and if so, goes to the verify-3 routine described below, blocks 1156 and 1160.

Figure 21:
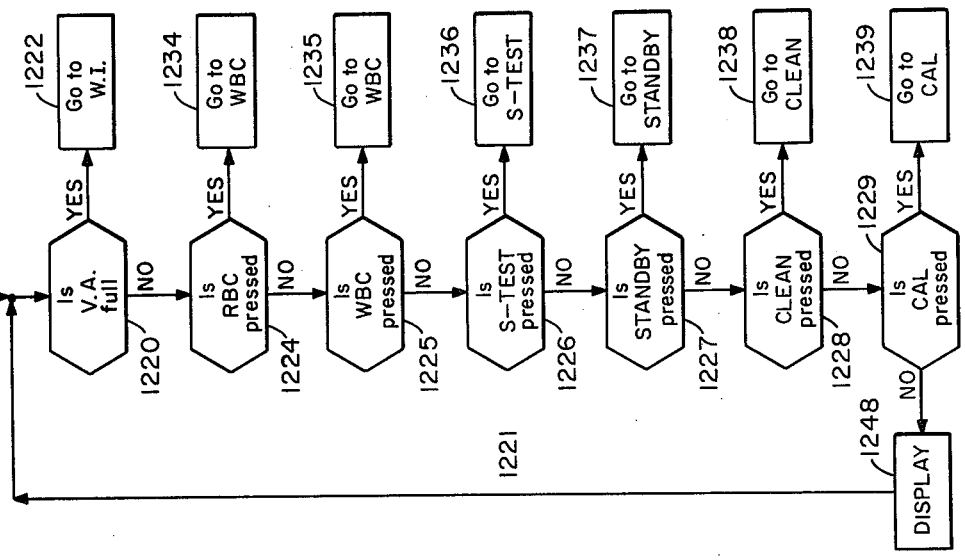
FIG. 21 is a flow diagram showing the steps carried out by the invention during a verify-3 routine.
Figure 20:
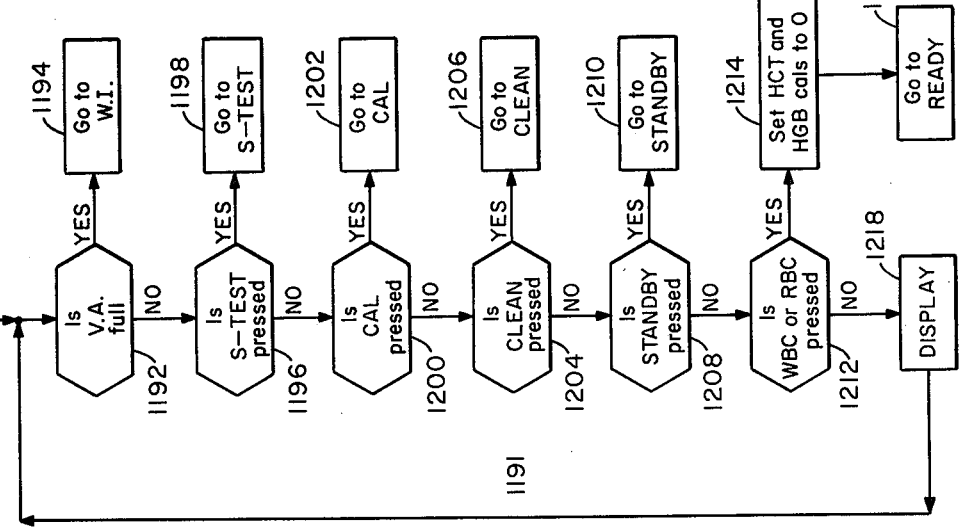
FIG. 20 is a flow diagram showing the steps carried out by the invention during a verify-2 routine.
Figure 19:
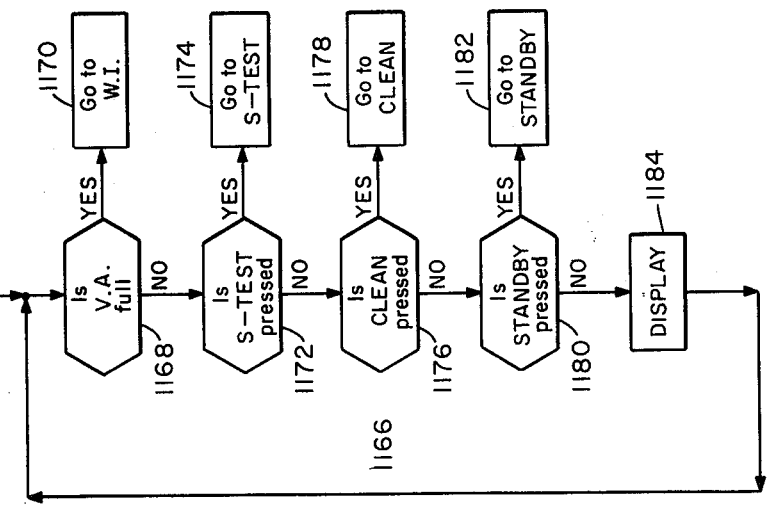
FIG. 19 is a flow diagram showing the steps carried out by the invention during a verify-1 routine.

FIGS. 19 through 21 show the verify routines performed by the instrument after the second occurrence of a malfunction during a cycle. These verify routines display to the operator information indicating the malfunction which occurred and corrective action which is appropriate, and only allow an operator to return to the proper cycles.

Referring to FIG. 19, the verify-1 routine is shown in detail. The processor first resets the TIME register, block 1164. The processor next enters loop 1156 which is repeated until the until the operator presses an allowed button.

First, the vacuum accumulator is checked, 1168, and if the vacuum accumulator is full, the processor goes to the waste interrupt routine, block 1170. Since the pass-check routine goes to the verify-1 routine only if the instrument was previously performing a self-test cycle, the instrument only allows the operator to attempt to repeat a self-test cycle, go to standby mode, or perform a clean cycle in preparation to turning off the machine. Accordingly, the processor first checks to determine if front panel self-test button 91 has been pressed, block 1172, and if so, goes to the self-test cycle, block 1174. Next the instrument checks to determine if front panel clean button 97 has been pressed by the operator, block 1176, and if so, goes to the clean cycle, block 1178. The instrument then checks to determine if front panel standby button 96 has been pressed, block 1180, and if so, goes to the standby cycle, block 1182. If the operator has not pressed a permited front panel button, the instrument will display the malfunction and corrective action messages previously loaded into the display message tables, block 1184. The processor then returns to block 1168 and the steps of loop 1166 are repeated.

If the instrument was repeating a calibration cycle when the malfunction was detected, the pass-check routine will jump to the verify-2 routine shown in FIG. 20. The instrument first resets the TIME register, block 1190. The processor then proceeds to loop 1191 which is repeated until the operator presses a front panel button. First, vacuum accumulator 46 is checked, block 1192; and if it is full, the processor goes to the waste interrupt routine, block 1194. Next the processor sequentially checks the front panel self-test, calibrate, clean, and standby buttons, block 1196, 1200, 1204 and 1208. If the processor determines that any of these buttons are pressed, it proceeds to the appropriate cycle, blocks 1198, 1202, 1206 and 1210.

The processor next checks to determine if the front panel WBC or RBC buttons are pressed, block 1212. If either of these buttons are pressed, the processor sets the calibration values for HCT and HGB measurements to zero, block 1214, and then goes to ready mode, block 1216. This allows an operator to determine the cell counts measured during either a WBC or an RBC sample run since the circuitry necessary therefor has been previously successfully checked out during the self-test cycle. The HCT and HGB values which are measured during WBC and RBC sample runs, and which require the successful completion of of a calibration cycle in order to be accurately measured, are not displayed to the operator. This prevents an operator from forgetting that a calibration cycle has not been carried out and inadvertently making incorrect measurements. From the ready state, the operator may then choose to perform either an RBC or a WBC sample run during which only cell count measurements will be made.

If no front panel button has been pressed by the operator, the instrument displays the malfunction and corrective action messages to the operator, block 1218. The processor then returns to block 1192 and repeats the steps of loop 1191.

FIG. 21 shows the steps performed by the processor in carrying out the verify-3 routine. Since the pass-check routine will only jump to the verify-3 routine if the processor was attempting a WBC or RBC sample run, the instrument permits the operator to return to any cycle or mode. To carry out the verify-3 routine, the processor first checks to determine if vacuum accumulator is full, block 1220; and if the vacuum accumulator is full, the instrument goes to the waste interrupt routine, block 1222. Otherwise, the processor sequentially checks the RBC, WBC, self-test, standby, clean and calibrate front panel buttons, blocks 1224 through 1229. If the instrument detects that the operator has pressed a front panel button, the instrument proceeds to the appropriate cycle, blocks 1234 through 1239. If no front panel button has been depressed, the instrument displays the malfunction and corrective action messages previously loaded into the display message tables, block 1248. The processor then returns to block 1220 and repeats the steps of loop 1221.

If the operator is not going to perform a sample run for a period of time exceeding ten minutes but does not wish to have to repeat the calibration and self-test cycles, he may put the instrument into standby mode. This is done by immersing sample probe 30 in a container of the deionized water and pressing the front panel standby button. Referring to FIG. 22, the steps carried out by the instrument in going to standby mode are explained. First, the processor resets the TIME register, block 1250. If vacuum accumulator 46 is full, block 1252, the instrument goes to the waste interrupt routine, block 1254. Otherwise, the instrument opens prime valve 48 and closes vent 51, block 1256, drawing the deionized water through the prime path. This is done for five seconds, block 1258. Prime valve 48 is closed, block 1260; and vacuum pump 32 is turned off, block 1264, although the residual vacuum in vacuum accumulator 46 continues to draw water down volumetric tube 54.

After the prime path and volumetric tube 54 have been filled with the deionized water, the instrument displays to the operator that it is in standby mode, block 1270, the instrument next repeatedly performs the procedure shown in block 1272 to allow the operator to leave standby mode by pressing a button corresponding with a permitted procedure, depending upon whether the self-test and/or calibration cycles have been performed. The "STANDBY" message displayed by the instrument while in standby mode remains on front panel display 149 after block 1270 has been performed, and the procedures within block 1272 do not branch to the display routine. Accordingly, the ten minute alarm to the operator initiated by the display routine will not be activated when the instrument is in standby mode.

Within block 1272 the processor first checks to determine if a calibration has been carried out, block 1274. If a calibration cycle has been successfully completed, the processor next checks to determine whether the RBC front panel button 93 or the WBC front panel button 95 has been pressed, blocks 1276 and 1278. If either button has been pressed, the processor proceeds to the appropriate cycle, blocks 1280 and 1282.

If the instrument has not been calibrated, the processor bypasses blocks 1276 and 1278, proceeding to block 1284 where the processor determines whether a self-test cycle has been performed. This prevents an operator from trying to carry out an RBC or WBC sample run unless the instrument has been calibrated. If the instrument has performed a self-test, the processor goes from block 1284 to block 1286 where the front panel calibration button is checked and if this button is pressed, the instrument performs a calibrate cycle, block 1288. Otherwise, the instrument tests only the remaining buttons.

If a self-test procedure has not been carried out, the only front panel buttons to which the instrument will be responsive are the self-test and clean buttons. Accordingly, the processor checks front panel self-test button 91, block 1290, and if it is pressed goes to the self-test cycle, block 1292. If the self-test button has not been pressed, the processor checks the front panel clean button 97, block 1294, and if this button is pressed, proceeds to perform a clean cycle, block 1296. Otherwise, the instrument returns to block 1274 and repeats the procedures in block 1272.

When the operator has finished running blood samples, a clean cycle is performed in preparation to turning the instrument off. Referring to FIG. 23, an operator initiates a clean cycle by immersing sample probe 30 in cleaning solution and pressing the front panel clean button 97. The instrument responds by resetting the TIME register, block 1300, and displaying "CLEANING" to the operator on the front panel display while the cleaning fluid is being aspirated into the instrument, block 1302. Next the instrument empties vacuum accumulator 46, block 1304. The instrument next opens prime valve 48 and closes vent 51, pulling the cleaning fluid through the prime path, block 1306. After five seconds, prime valve 48 is closed, causing the cleaning fluid to be drawn through the transducer and through volumetric tube 54, block 1308. After waiting five seconds, block 1310, the instrument proceeds to block 1312 and displays to the operator the message "TURN SYSTEM OFF". The processor then turns off vacuum pump 32 and disables the front panel controls, block 1314;

Various modifications and alternate implementations which do not depart from the true scope of the invention will be apparent to those versed in the art. Accordingly, it is not intended to limit the invention by what has been particularly shown and described, except as indicated in the appended claims.

What is claimed is:

1. A blood analysis system adapted to receive and analyze a blood sample comprising:
   transducer means responsive to the blood sample for providing electrical pulses representative of blood cells passing therethrough;
   a fluid path coupled to the transducer means and through which the blood sample flows after flowing through the transducer means;
   first sensing means located along the fluid path for providing a first signal representative of the flow of a first predetermined sample volume through the fluid path;
   second sensing means located along the fluid path for providing a second signal representative of the flow of a second predetermined sample volume through the fluid path;
   means responsive to the electrical pulses and to the first signal for providing a first count of blood cell concentration in the first predetermined sample volume;
   the means for providing said first representation being further responsive to the electrical pulses and to the second signal for providing a second count of the blood cell concentration in the second predetermined sample volume;
   means for comparing the first and the second counts to provide a determination of when said first and second counts differ by less than a predetermined difference; and
   means operative only upon said determination and responsive to said first and second counts for providing as an output an average of said counts.

2. The system of claim 1 wherein the first and second sensing means include:
reference means for setting an electrical threshold;
said transducer means being operative to provide said electrical pulses with an amplitude representation of blood cell size;
comparator means for providing an output indication when the amplitude of the electrical pulses from the transducer means exceeds the threshold set by the reference means.

3. The system of claim 2 further comprising:
a second fluid path;
means for selectively conveying the blood sample through the second fluid path;
means associated with the second fluid path for producing a signal representative of hemoglobin concentration of the blood sample conveyed therethrough.

4. The system of claim 2 further comprising:
means for summing the amplitudes of electrical pulses from the transducer means produced by the flow therethrough of blood cells and for determining the average of the summed amplitudes to produce a signal representative of mean cell volume of the cells passing through the transducer.

5. The system of claim 4 further comprising test means including:
means for producing test pulses;
means for applying the test pulses at an output of the transducer means to simulate the electrical pulses produced thereby;
means coupled to said test means for causing a predetermined number of test pulses to be produced at predetermined intervals;
means for comparing the signal representative of mean cell volume, produced in response to the simulated electrical pulses from the transducer means, with a second predetermined signal and for producing a signal representative of the difference therebetween;
means for determining whether said difference therebetween is within predetermined tolerances, and for providing a signal upon exceedance of the predetermined tolerances representative thereof;
means for comparing at least one of said first and second representations of the number of blood cells, produced in response to the simulated electrical pulses representative of blood cells passing through the transducer means, with a signal representative of the number of pulses produced by the test means to provide a signal representative of the difference therebetween;
means for determining if the difference therebetween exceeds predetermined limits and for producing a signal, upon exceedance of the limits, representative thereof.

6. The system of claim 5 further comprising:
second input means for producing signals representative of a hemoglobin concentration;
switch means for providing a calibrate signal;
means responsive to said calibrate signal for comparing said signal representative of the hemoglobin concentration of the blood passing through said second fluid path with the signals from the second input means to determine the difference therebetween, and upon exceedance of a predetermined tolerance by this difference, for computing a hemoglobin correction factor equal to the quotient of the hemoglobin concentration indicated by the signals from the first input means divided by the hemoglobin concentration indicated by the signals from said means associated with the second fluid path; and
means, operative in the absence of a calibrate signal, for multiplying said signal representative of the hemoglobin concentration factor to produce a corrected signal representative of hemoglobin concentration of a blood sample flowing through the second fluid path.

7. The system of claim 5 further comprising:
means for suppressing signals representative of the blood cell concentration or mean cell volume prior to operation of said test means and calibration means.

8. The system of claim 1 further comprising:
means for measuring a first flow time corresponding to the time of flow of the first predetermined volume through the first fluid path and for measuring a second flow time corresponding to the time of flow of the second predetermined volume through the first fluid path; and
means for comparing the first and second flow times each with respective upper and lower limits, and for providing a malfunction signal if either of said first or second flow times falls outside of said respective upper and lower limits.

9. A blood analysis system adapted to receive and analyze a blood sample comprising:
transducer means for providing, upon flow of said blood sample therethrough, electrical pulses representative of blood cells passing therethrough;
a first fluid path coupled to said transducer means and through which the blood sample is caused to flow after flowing through said transducer means;
first sensing means located along said first fluid path for providing a first signal representative of a first sample flow corresponding to the flow of a first predetermined volume through said first fluid path;
second sensing means located along said first fluid path for providing a second signal representative of a second sample flow corresponding to the flow of a second predetermined volume through said fluid path;
a second fluid path bypassing said transducer means and said first fluid path;
means associated with the second fluid path for determining hemoglobin concentration of a blood sample flowing therethrough;
a vacuum accumulator;
a vacuum pump connected to vacuum accumulator for removing air therefrom to produce a reduced air pressure in said vacuum accumulator;
means for coupling said vacuum accumulator to said first fluid path and to said second fluid path so that the reduced air pressure in the vacuum accumulator is operative to cause fluids present in said first fluid path to flow therethrough and into said vacuum accumulator;
means for pressurizing the vacuum accumulator to expel therefrom fluids which have accumulated therein;
means for selectively applying the reduced pressure in the vacuum accumulator to said second fluid path to cause fluids present in the second fluid path to flow therethrough and into the vacuum accumulator;

counting means responsive to said electrical pulses and to said first signal for providing a first count of the number of blood cells in said first sample flow;

the counting means being further responsive to the electrical pulses and to said second signal for providing a second count of the number of blood cells in said second sample flow;

means for comparing the first and second counts to determine whether said counts agree within a predetermined tolerance; and means responsive to said first and second counts for providing an average of said counts as an output only if the first and second counts agree to within the predetermined tolerance.

10. The system of claim 9 wherein the counting means includes:

reference means for setting an electrical threshold; and comparator means for providing an output indication when the amplitude of the electrical pulses from the transducer means exceeds the threshold set by the reference means.

11. The system of claim 16 further comprising:

means for summing the amplitude of electrical pulses from the transducer means produced by the flow therethrough of blood cells and for determining the average of the summed amplitudes to produce a signal representative of mean cell volume of the cells passing through the transducer.

12. A blood analysis system adapted to receive and analyze a blood sample comprising:

transducer means responsive to the blood sample for providing electrical pulses representative of blood cells passing therethrough;

a fluid path coupled to the transducer means and through which the blood sample flows after flowing through the transducer means;

first sensing means located along the fluid path for providing a first signal representative of the flow of a first predetermined sample volume through the fluid path;

second sensing means located along the fluid path for providing a second signal representative of the flow of a second predetermined sample volume through the fluid path;

said first and second sensing means including:

reference means for setting an electrical threshold;

said transducer means being operative to provide said electrical pulses with an amplitude representation of blood cell size; and comparator means for providing an output indication when the amplitude of the electrical pulses from the transducer means exceeds the threshold set by the reference means;

means responsive to the electrical pulses and to the first signal for providing a first representation of blood cell concentration in the first predetermined sample volume;

the means for providing said first representation being further responsive to the electrical pulses and to the second signal for providing a second representation of the blood cell concentration in the second predetermined sample volume;

means for comparing the first and the second representations to provide a determination of when said first and second representations differ by less than a predetermined difference;

means operative only upon said determination and responsive to said first and second representations for providing an output signal representative of blood cell concentration of the blood sample; and means for summing the amplitudes of electrical pulses from the transducer means produced by the flow therethrough of blood cells and for determining the average of the summed amplitudes to produce a signal representative of mean cell volume of the cells passing through the transducer.

13. The system of claim 12 further comprising:

means for multiplying the signal representative of the mean cell volume by a signal representative of the blood cell count of the sample to produce a signal representative of the hematocrit value of the blood sample.

14. The system of claim 13 wherein the means for providing the first and second representations include:

counter means for counting output pulses from the comparator means; and means for reading and for storing at respective first and second locations the value accumulated in the counter during the flow of said first predetermined volume and the value accumulated by the counter during the flow of said second predetermined volume.

15. The system of claim 14 wherein the means for summing includes an analog-to-digital converter;

the electrical pulses from the transducer being applied to the converter for transformation into digital representations thereof;

accumulator means for reading the digital representations and for accumulating an algebraic sum thereof;

averaging means operative after the flow of said predetermined volumes for dividing the accumulated sum by corresponding representation of the number of blood cells which produced that sum.

16. The system of claim 12 further comprising calibration means, including:

input means for producing signals representative of a predetermined mean cell volume;

switch means for providing a calibrate signal;

means responsive to said calibrate signal for computing a mean cell volume correction factor equal to the quotient of the mean cell volume value indicated by the signals from the first input means divided by the mean cell volume of the cells passing through the transducer; and operative in the absence of a calibrate signal, means for multiplying said signal representative of the mean cell volume of the cells passing through the transducer by the mean cell volume correction factor to produce a signal representative of corrected mean cell volume of the cells passing through the transducer.

17. A blood analysis system adapted to receive and analyze a blood sample comprising:

transducer means responsive to the blood sample for providing electrical pulses representative of blood cells passing therethrough;

a fluid path coupled to the transducer means and through which the blood sample flows after flowing through the transducer means;

first sensing means located along the fluid path for providing a first signal representative of the flow of a first predetermined sample volume through the fluid path;

second sensing means located along the fluid path for providing a second signal representative of the flow of a second predetermined sample volume through the fluid path;

means responsive to the electrical pulses and to the first signal for providing a first representation of blood cell concentration in the first predetermined sample volume;

the means for providing said first representation being further responsive to the electrical pulses and to the second signal for providing a second representation of the blood cell concentration in the second predetermined sample volume;

means for comparing the first and the second representations to provide a determination of when said first and second representations differ by less than a predetermined difference;

means operative only upon said determination and responsive to said first and second representations for providing an output signal representative of blood cell concentration of the blood sample;

means for measuring a first flow time corresponding to the time of flow of the first predetermined volume through the first fluid path and for measuring a second flow time corresponding to the time of flow of the second predetermined volume through the first fluid path; and means for comparing the first and second flow times each with respective upper and lower limits, and for providing a malfunction signal if either of said first or second flow times falls outside of said respective upper and lower limits.

18. The system of claim 17 further including means for determining said upper and lower limits of each of said first and second flow times, including:
   means for storing representations of said first and second flow times of a blood sample measured by said means for measuring and
   means for calculating said upper and lower limits for each of said first and second flow times by respectively increasing and decreasing each of said first and second flow times by a specified percentage to produce said respective upper and lower time limits for said first and said second flow times.

19. The system of claim 18 wherein the specified percentage is 10%.

20. A blood analysis system adapted to receive and analyze a blood sample comprising:
   transducer means for providing, upon flow of said blood sample therethrough, electrical pulses representative of blood cells passing therethrough;
   a first fluid path coupled to said transducer means and through which the blood sample is caused to flow after flowing through said transducer means;
   first sensing means located along said first fluid path for providing a first signal representative of a first sample flow corresponding to the flow of a first predetermined volume through said first fluid path;
   second sensing means located along said first fluid path for providing a second signal representative of a second sample flow corresponding to the flow of a second predetermined volume through said fluid path;
   a second fluid path bypassing said transducer means and said first fluid path;
   means associated with the second fluid path for determining hemoglobin concentration of a blood sample flowing therethrough;

a vacuum accumulator;
   a vacuum pump connected to vacuum accumulator for removing air therefrom to produce a reduced air pressure in said vacuum accumulator;
   means for coupling said vacuum accumulator to said first fluid path and to said second fluid path so that the reduced air pressure in the vacuum accumulator is operative to cause fluids present in said first fluid path to flow therethrough and into said vacuum accumulator;
   means for pressurizing the vacuum accumulator to expel therefrom fluids which have accumulated therein;
   means for selectively applying the reduced pressure in the vacuum accumulator to said second fluid path to cause fluids present in the second fluid path to flow therethrough and into the vacuum accumulator;
   counting means responsive to said electrical pulses and to said first signal for providing a first representation of the number of blood cells in said first sample flow;
   said counting means including:
   reference means for setting an electrical threshold; and
   comparator means for providing an output indication when the amplitude of the electrical pulses from the transducer means exceeds the threshold set by the reference means;
   the counting means being further responsive to the electrical pulses and to said second signal for providing a second representation of the number of blood cells in said second sample flow;
   means for comparing the first and second representations to determine whether said representations agree within a predetermined tolerance;
   means responsive to said first and second representations for providing an output signal representative of blood cell count only if the first and second representations agree to within the predetermined tolerance;
   means for summing the amplitude of electrical pulses from the transducer means produced by the flow therethrough of blood cells and for determining the average of the summed amplitudes to produce a signal representative of mean cell volume of the cells passing through the transducer.

21. The system of claim 20 wherein the counting means further includes:
   a counter for counting output pulses from the comparator means; and
   a digital processor;
   the value accumulated in the counter during the first sample flow being read by the digital processor and stored at a first location therein, and the value accumulated in the counter during the second sample flow being read by the digital processor and stored at a second location therein.

22. The system of claim 21 wherein the means for summing includes:
   an analog-to-digital converter;
   the electrical pulses from the transducer being applied to the converter for transformation into digital representations thereof;
   the digital processor being operative to read the digital representations and provide a summation of the read digital representations;

the digital processor being further operative for dividing the summation provided during one of said first and second sample flows by the number of blood cells which produce that summation.

23. The system of claim 22 further comprising:

input means for producing signals representative of a predetermined mean cell volume:

switch means for providing a calibrate signal to the digital processor;

the digital processor being responsive to said calibrate signal to compare the signal representative of the mean cell volume of the cells passing through the transducer means with the signals from the first imput means to determine the difference therebetween;

the digital processor being further operative upon exceedance of a predetermined tolerance by the difference in the signals representative of the mean cell volumes to provide an output signal indicative thereof;

the digital processor being operative upon a nonexceedance of the predetermined tolerance for computing a mean cell volume correction factor equal to the quotient of the perdetermined mean cell volume value indicated by the signals from the first input means divided by the mean cell volume of the cells passing through the transducer means.

* * * * *

UNITED STATES PATENT AND TRADEMARK OFFICE
CERTIFICATE OF CORRECTION

PATENT NO. : 4,093,849
DATED : June 6, 1978
INVENTOR(S) : Robert Baxter, Jr. et al It is certified that error appears in the above-identified patent and that said Letters Patent are hereby corrected as shown below:

Column 2, line 57, "being" should be --begin--.

Column 8, line 61, "110" should be --100--.

Column 9, line 62, "154" second occurrence should be --156--.

Column 30, line 52, "sotred" should be --stored--.

Signed and Sealed this

Thirteenth Day of February 1979

[SEAL]

Attest:

RUTH C. MASON
*Attesting Officer*

DONALD W. BANNER
*Commissioner of Patents and Trademarks*